United States Patent
Beckmann et al.

(10) Patent No.: US 9,944,719 B2
(45) Date of Patent: Apr. 17, 2018

(54) DUAL TARGETING

(71) Applicant: DUTALYS GMBH, Vienna (AT)

(72) Inventors: Roland Beckmann, Vienna (AT); Kristian Jensen, Landshut (DE)

(73) Assignee: Hoffman-La Roche Inc., Little Falls, NJ (US)

(*) Notice: Subject to any disclaimer, the term of this patent is extended or adjusted under 35 U.S.C. 154(b) by 88 days.

(21) Appl. No.: 14/650,083

(22) PCT Filed: Dec. 5, 2013

(86) PCT No.: PCT/EP2013/003688
§ 371 (c)(1),
(2) Date: Jun. 5, 2015

(87) PCT Pub. No.: WO2014/086496
PCT Pub. Date: Jun. 12, 2014

(65) Prior Publication Data
US 2015/0315295 A1    Nov. 5, 2015

(30) Foreign Application Priority Data
Dec. 5, 2012  (EP) .................................. 12008154

(51) Int. Cl.
  C40B 40/10  (2006.01)
  C07K 16/46  (2006.01)
  C12N 15/10  (2006.01)
  C07K 16/22  (2006.01)
  C07K 16/24  (2006.01)

(52) U.S. Cl.
  CPC ............ *C07K 16/468* (2013.01); *C07K 16/22* (2013.01); *C07K 16/243* (2013.01); *C07K 16/248* (2013.01); *C12N 15/1037* (2013.01); *C07K 2317/31* (2013.01); *C07K 2317/565* (2013.01); *C07K 2317/92* (2013.01); *C40B 40/10* (2013.01)

(58) Field of Classification Search
None
See application file for complete search history.

(56) References Cited

FOREIGN PATENT DOCUMENTS

| CN | 1678634 A | 10/2005 |
| JP | 2008-518619 | 6/2008 |
| WO | 2004003019 | 1/2004 |
| WO | 2006/050491 A2 | 5/2006 |
| WO | 2008027236 A2 | 3/2008 |
| WO | 2012163520 A1 | 12/2012 |

OTHER PUBLICATIONS

Bostrom Jenny et al: "Variants of the antibody herceptin that interact with HER2 and VEGF at the antigen binding site", Science, American Association for the Advancement of Science, vol. 323, No. 5921, Mar. 20, 2009 (Mar. 20, 2009), pp. 1610-1614.
International Search Report and Written Opinion issued in PCT/EP2013/003688 dated Mar. 27, 2014 (13 pages).
Office Action issued in CN 201380063422.7 dated May 15, 2017 (8 pages and translation 5 pages).
Office Action issued in JP 2015-545695 dated Oct. 17, 2016 (10 pages and translation 11 pages).

*Primary Examiner* — Christian C Boesen
(74) *Attorney, Agent, or Firm* — Prismatic Law Group, PLLC

(57) ABSTRACT

The present invention relates to antibody-based dual targeting molecules, and to methods for generating such dual targeting molecules, including a library-based approach.

4 Claims, 20 Drawing Sheets

Figure 1: Lists of preferred residues

A: List of the preferred CDR positions, of which all positions or a subset should be diversified to form the two binding regions in the most preferred dual targeting antibodies (all numbering according to Kabat)

Group "Lib1" = VL24, VL25, VL26, VL27, VL28#, VL29##, VL93, VL94, VL95§, VL95a§, VL95b§, VH58, VH59, VH60, VH61, VH62, VH63, VH64, VH65

Group "Lib1_A" = VL24, VL25, VL26, VL27, VL28#, VL29##, VL92, VL93, VL94, VL95§, VL95a§, VL95b§, VL97, VH58, VH59, VH60, VH61, VH62, VH63, VH64, VH65

Group "Lib2" = VH26*, VH27*, VH28*, VH29*, VH30*, VH31, VH32, VH94, VH96, VH97, VH98, VH99, VH102, VL49, VL53, VL54, VL55, VL56

\# This residue having number 28 in the Kabat nomenclature assumes that CDR-L1 length is 11; if the length is 10, then the residue number is 29; if the length is 12 or more, then the residue number is 27a.
\#\# This residue having number 29 in the Kabat nomenclature assumes that CDR-L1 length is 11; if the length is 10, then the residue number is 30; if the length is 12, then the residue number is 28; if the length is 13 or more, then the residue number is 27b.
$ Only in case of libraries comprising Vlambda light chains
* These residues are not included in the Kabat definition of CDR residues (Kabat et al., 1991), but they are included in the Chothia definition of CDR residues (Chothia et al., 1992), and they are included in our definition of CDR residues.
** These residues are not included in the Kabat definition of CDR residues (Kabat et al., 1991), but they are included in the Contact definition of CDR residues (MacCallum et al., 1996), and they are included in our definition of CDR residues.

B: List of preferred enhancing positions that can be diversified in some library designs to enhance the properties of the two binding regions in the novel dual targeting antibodies (all numbering according to Kabat)

Group "Lib1E" = VL1, VL2, VL3, VL69, VL70, VL100, VH46
Group "Lib1E_A" = VL1, VL2, VL3, VL4, VL69, VL70, VL100, VH46
Group "Lib2E" = VH1, VH2, VH3, VH25, VH76, VH105, VL45, VL57, VL58
Group "Lib2E_A" = VH1, VH2, VH3, VH25, VH76, VH105, VL45, VL57, VL58, VL60

C: List of preferred CDR positions, of which all positions or a subset is preferably left invariant or subjected to restricted diversification in both Lib1 and Lib2 library designs, to create an antibody core region that allows the two binding regions comprising Lib1 and Lib2 residues to behave independently (all numbering according to Kabat)

VL residues = VL32, VL33, VL34, VL50, VL51, VL52, VL89, VL90, VL91, VL96
VH residues = VH33, VH34, VH35, VH50, VH51, VH52, VH52a, VH52b if present, VH52c if present, VH53, VH54, VH55, VH57, VH95, and the residue directly before VH101 (which can have variable numbering depending on HCDR3 length)

Figure 3: Library Designs x = diversified position

Vkappa Libraries:

```
              10         20         30         40         50         60         70         80         90        100
              ....|....|....|....|....|....|....|....|....|....|....|....|....|....|....|....|....|....|....|....|
Dummy 1 VK    DIQMTQSPSSLSASVGDRVTITCRASQSISSYLAWYQQKPGKAPKLLIYAASSLYSGVPSRFSGSGSGTDFTLTISSLQPEDFATYYCQQYSSLPYTFGQGTKVEIKR
```

Diversified VL Domain (SEQ-ID NO: 18):
```
Lib D1L1 VK   XXQMTQSPSSLSASVGDRVTITCRXXXXXXSSYLAWYQQKPGKAPKLLIYAASSLYSGVPSRFSGSGSGXXFTLTISSLQPEDFATYYCQQYSXLPYTFGQGTKVEIKR
```

Diversified VL Domain (SEQ-ID NO: 19):
```
Lib D1L2 VK   XXXMTQSPSSLSASVGDRVTITCRXXXXXXSSYLAWYQQKPGKAPKLLIYAASSLYSGVPSRFSGSGSGXXFTLTISSLQPEDFATYYCQQYXXPYTFGQGTKVEIKR
```

```
              10         20         30         40         50         60         70         80         90        100       110
              ....|....|....|....|....|....|....|....|....|....|....|....|....|....|....|...a|.abc.|....|....|....|....|....|
Dummy 1 VH    EVQLVESGGGLVQPGGSLRLSCAASGFTFSSYAMSWIRQAPGKGLEWIGQISGSGGSTYYNDVLGRFTISRDNSKNTLYLQMNSLRAEDTAVYYCARDSGYFDIWGQGTLVTVSS
```

Diversified VH Domain (SEQ-ID NO: 20):
```
Lib D1H1 VH   EVQLVESGGGLVQPGGSLRLSCAASGFTFSSYAMSWIRQAPGKGLEWIGQISGSGGSTXYXXXXXGRFTISRDNSKNTLYLQMNSLRAEDTAVYYCARDSGYFDIWGQGTLVTVSS
```

Diversified VH Domain (SEQ-ID NO: 21):
```
Lib D1L2 VH   EVQLVESGGGLVQPGGSLRLSCAASGFTFSSYAMSWIRQAPGKGLXWIGQISGSGGSTXYXXXXXGRFTISRDNSKNTLYLQMNSLRAEDTAVYYCARDSGYFDIWGQGTLVTVSS
```

```
              10         20         30         40         50         60         70         80         90        100
              ....|....|....|....|....|....|....|....|....|....|....|....|....|....|....|....|....|....|....|....|
Dummy 1 VK    DIQMTQSPSSLSASVGDRVTITCRASQSISSYLAWYQQKPGKAPKLLIYAASSLYSGVPSRFSGSGSGTDFTLTISSLQPEDFATYYCQQYSSLPYTFGQGTKVEIKR
```

Diversified VL Domain (SEQ-ID NO: 22):
```
Lib D1H1 VK   DIQMTQSPSSLSASVGDRVTITCRASQSISSYLAWYQQKPGKAPKLLIXAASXLXXXXXPSRFSGSGSGTDFTLTISSLQPEDFATYYCQQYSSLPYTFGQGTKVEIKR
Lib D1H2 VK   DIQMTQSPSSLSASVGDRVTITCRASQSISSYLAWYQQKPGKAPKLLIXAASXLXXXXXPSRFSGSGSGTDFTLTISSLQPEDFATYYCQQYSSLPYTFGQGTKVEIKR
```

Diversified VL Domain (SEQ-ID NO: 23):
```
Lib D1H3 VK   DIQMTQSPSSLSASVGDRVTITCRASQSISSYLAWYQQKPGKAPKLLIXAASXLXXXXXPSRFSGSGSGTDFTLTISSLQPEDFATYYCQQYSSLPYTFGQGTKVEIKR
```

```
              10         20         30         40         50         60         70         80         90        100       110
              ....|....|....|....|....|....|....|....|....|....|....|....|....|....|....|...a|.abc.|....|....|....|....|....|
Dummy 1 VH    EVQLVESGGGLVQPGGSLRLSCAASGFTFSSYAMSWIRQAPGKGLEWIGQISGSGGSTYYNDVLGRFTISRDNSKNTLYLQMNSLRAEDTAVYYCARDSGYFDIWGQGTLVTVSS
```

Figure 3: Library Designs (continued)

Diversified VH Domain (SEQ-ID NO: 24):

```
Lib D1H1 VH  XXQLVESGGGLVQPGGSLRLSCAAXGFXFSXYAMSWIRQAPGKGLEWIGQISGSGGSTYYNDNVLGRFTISRDNSKXTLYLQMNSLRAEDTAVYYCAXDSGYFDXWGQGTLVTVSS
```

Diversified VH Domain (SEQ-ID NO: 25):

```
Lib D1H2 VH  XXXLVESGGGLVQPGGSLRLSCAAXGXXXSXYAMSWIRQAPGKGLEWIGQISGSGGSTYYNDNVLGRFTISRDNSKXTLYLQMNSLRAEDTAVYYCARDSGYFDXWGQGTLVTVSS
```

Diversified VH Domain (SEQ-ID NO: 26):

```
Lib D1H3 VH  XXQLVESGGGLVQPGGSLRLSCAASGXXXSXXAMSWIRQAPGKGLEWIGQISGSGGSTYYNDNVLGRFTISRDNSKNTLYLQMNSLRAEDTAVYYCARDXGXFDXWGQGTLVTVSS
```

Vlambda Libraries:

```
                         10        20        30        40        50        60        70        80        90       100       110
                ....|....|....|....|....|....|....|....|....|....|....|....|..ab..|....|....|....|....|....|....|..ab..|....|....|....|
Dummy 2 VL      SSVLTQPPSVSGAPGQRVTISCSGSSSNIGSNTVSWYQQLPGTAPKLLIYGNNNRPSGVPDRFSGSKSGTSASLAITGLQSEDEADYYCAAWDDSLNGYVFGTGTKVTVL
Lib D2L1 VL     XXVLTQPPSVSGAPGQRVTISCSGSGXXXXNIGXNTVSWYQQLPGTAPKLLIYGNNNRPSGVPDRFSGSKSGTSASLAITGLQSEDEADYYCAAWDXXXXGYVFGTGTKVTVL 10        20        30        40        50        60        70        80        90       100
                ....|....|....|....|....|....|..ab..|....|....|....|....|....|....|....|....|....|....|....|....|..abc.|....|....|
Dummy 2 VH      EVQLVESGGGLVQPGGSLRLSCAASGFTFSSNYMSWVRQAPGKGLEWVGTISGSGGSTYYNDNVLGRFTISRDNSKNTLYLQMNSLRAEDTAVYYCARTSSGYFDYWGQGTLVTVSS
Lib D2H1 VH     EVQLVESGGGLVQPGGSLRLSCAASGFTFSSNYMSWVRQAPGKGLEWVGTISGSGGSTYXXXXGRFTISRDNSKNTLYLQMNSLRAEDTAVYYCARTSSGYFDYWGQGTLVTVSS 10        20        30        40        50        60        70        80        90       100
                ....|....|....|....|....|....|..ab..|....|....|....|....|....|....|....|....|....|....|....|....|..abc.|....|....|
Dummy 2 VL      SSVLTQPPSVSGAPGQRVTISCSGSSSNIGSNTVSWYQQLPGTAPKLLIYGNNXRXXXXPDRFSGSKSGTSASLAITGLQSEDEADYYCAAWDDSLNGYVFGTGTKVTVL
Lib D2H1 VL     SSVLTQPPSVSGAPGQRVTISCSGSSSNIGSNTVSWYQQLPGTAPKLLIXGNNXRXXXXPDRFSGSKSGTSASLAITGLQSEDEADYYCAAWDDSLNGYVFGTGTKVTVL 10        20        30        40        50        60        70        80        90       100
                ....|....|....|....|....|....|....|....|....|....|....|....|....|....|....|....|....|....|....|..abc.|....|....|
Dummy 2 VH      EVQLVESGGGLVQPGGSLRLSCAASGFTFSSNYMSWVRQAPGKGLEWVGTISGSGGSTYYNDNVLGRFTISRDNSKNTLYLQMNSLRAEDTAVYYCARTSSGYFDYWGQGTLVTVSS
Lib D2H1 VH     XXQLVESGGGLVQPGGSLRLSCAASGXXYMSWVRQAPGKGLEWVGTISGSGGSTYYNDNVLGRFTISRDNSKNTLYLQMNSLRAEDTAVYYCAXTXXXGXFDXWGQGTLVTVSS
```

Figure 4: Examples of bi-specific antibodies

```
                        10         20         30         40         50         60         70         80         90        100
                        ....|....|....|....|....|....|....|....|....|....|....|....|....|....|....|....|....|....|....|....|
Dummy 1 VK              DTQMTQSPSSLSASVGDRVTITCRASQSISSYLAWYQQKPGKAPKLLIYAASSLYSGVPSRFSGSGSGTDFTLTISSLQPEDFATYYCQQYSSLPYTFGQGTKVEIKR
LG1 VK                  GIQMTQSPSSLSASVGDRVTITCRARWYISSYLAWYQQKPGKAPKLLIYAASSLYSGVPSRFSGSGSGKDFTLTISSLQPEDFATYYCQQYSELPYTFGQGTKVEIKR
HM2 VK                  DTQMTQSPSSLSASVGDRVTITCRASQSISSYLAWYQQKPGKAPKLLIFAASRLILNVPSRFSGSGSGTDFTLTISSLQPEDFATYYCQQYSELPYTFGQGTKVEIKR
DT3 VK                  GIQMTQSPSSLSASVGDRVTITCRARWYISSYLAWYQQKPGKAPKLLIFAASRLILNVPSRFSGSGSGKDFTLTISSLQPEDFATYYCQQYSELPYTFGQGTKVEIKR 10         20         30         40         50         60         70         80         90        100       110
                        ....|....|....|....|....|....|....|....|....|....|....|....|....|....|....|....|....|....|....|....|....|....|
Dummy 1 VH              EVQLVESGGGLVQPGGSLRLSCAASGFTFSSYAMSWIRQAPGKGLEWIGQISGSGGSTYYNDNVLGRFTISRDNSKNTLYLQMNSLRAEDTAVYYCARDSGYFDIWGQGTLVTVSS
LG1 VH                  EVQLVESGGGLVQPGGSLRLSCAASGFTFSSYAMSWIRQAPGKGLEWIGQISGSGGSTYYNDNVLGRFTISRDNSKNTLYLQMNSLRAEDTAVYYCARDSGYFDIWGQGTLVTVSS
HM2 VH                  WVQLVESGGGLVQPGGSLRLSCAARGFPFSHYAMSWIRQAPGKGLEWIGQISGSGGSTWYNHDIKGRFTISRDNSKNTLYLQMNSLRAEDTAVYYCARDSGYFDIWGQGTLVTVSS
DT3 VH                  WVQLVESGGGLVQPGGSLRLSCAARGFPFSHYAMSWIRQAPGKGLEWIGQISGSGGSTWYNHDIKGRFTISRDNSKNTLYLQMNSLRAEDTAVYYCARDSGYFDWWGQGTLVTVSS 10         20         30         40         50         60         70         80         90        100
                        ....|....|....|....|....|....|....|....|....|....|....|....|....|....|....|....|....|....|....|....|
Dummy 1 VK              DTQMTQSPSSLSASVGDRVTITCRASQSISSYLAWYQQKPGKAPKLLIYAASSLYSGVPSRFSGSGSGTDFTLTISSLQPEDFATYYCQQYSSLPYTFGQGTKVEIKR
IL6P VK                 NIQKTQSPSSLSASVGDRVTITCRALWHISSYLAWYQQKPGKAPKLLIYAASHLHYGVPSRFSGSGSGTDFTLTISSLQPEDFATYYCQQYSSLPYTFGQGTKVEIKR
VEGFP VK                DTQMTQSPSSLSASVGDRVTITCRASQSISSYLAWYQQKPGKAPKLLIYAASSLYSGVPSRFSGSGSGTDFTLTISSLQPEDFATYYCQQYSGLPYTFGQGTKVEIKR
VH6L VK                 NIQKTQSPSSLSASVGDRVTITCRALWHISSYLAWYQQKPGKAPKLLIYAASHLHYGVPSRFSGSGSGTDFTLTISSLQPEDFATYYCQQYSGLPYTFGQGTKVEIKR 10         20         30         40         50         60         70         80         90        100       110
                        ....|....|....|....|....|....|....|....|....|....|....|....|....|....|....|....|....|....|....|....|....|....|
Dummy 1 VH              EVQLVESGGGLVQPGGSLRLSCAASGFTFSSYAMSWIRQAPGKGLEWIGQISGSGGSTYYNDNVLGRFTISRDNSKNTLYLQMNSLRAEDTAVYYCARDSGYFDIWGQGTLVTVSS
IL6P VH                 EVQLVESGGGLVQPGGSLRLSCAASGFTFSSYAMSWIRQAPGKGLEWIGQISGSGGSTVYNYNVLGRFTISRDNSKNTLYLQMNSLRAEDTAVYYCARDSGYFDIWGQGTLVTVSS
VEGFP VH                YYQLVESGGGLVQPGGSLRLSCAADGFLFSGYAMSWIRQAPGKGLEWIGQISGSGGSTVYNYNVLGRFTISRDNSKNTLYLQMNSLRAEDTAVYYCARDTGYFDHWGQGTLVTVSS
VH6L VH                 YYQLVESGGGLVQPGGSLRLSCAADGFLFSGYAMSWIRQAPGKGLEWIGQISGSGGSTVYNYNVLGRFTISRDNSKNTLYLQMNSLRAEDTAVYYCARDTGYFDHWGQGTLVTVSS 10         20         30         40         50         60         70         80         90        100
                        ....|....|....|....|....|....|....|....|....|....|....|....|....|....|....|....|....|....|....|....|
GH6L VK                 ATQRTQSPSSLSASVGDRVTITCRALWHISSYLAWYQQKPGKAPKLLIYAASWLYWDVPSRFSGSGSGTDFTLTISSLQPEDFATYYCQQYSGLPYTFGQGTKVEIKR GH6L VH                 WVQLVESGGGLVQPGGSLRLSCAAKGALFSTYAMSWIRQAPGKGLEWIGQISGSGGSTVYNYNVLGRFTISRDNSKNTLYLQMNSLRAEDTAVYYCARDTGYFDHWGQGTLVTVSS
```

Figure 5: ELISA data of anti-MBP anti-GST dual targeting Fab clone DT3, using Dummy 1 Fab and irrelevant targets HEL and VEGF as controls Figure 6: Biacore™ data of anti-MBP / anti-GST dual targeting Fab clone DT3

Figure 6: Biacore™ data of anti-MBP / anti-GST dual targeting Fab clone DT3 (contd.)

Figure 7: Biacore™ analysis of parental and bi-specific antibodies against VEGF and IL6

Figure 7: Biacore™ analysis of parental and bi-specific antibodies against VEGF and IL6 (contd.)

Figure 7: Biacore™ analysis of parental and bi-specific antibodies against VEGF and IL6 (contd.)

A: Co-binding of GMCSF + Antibody + IL6

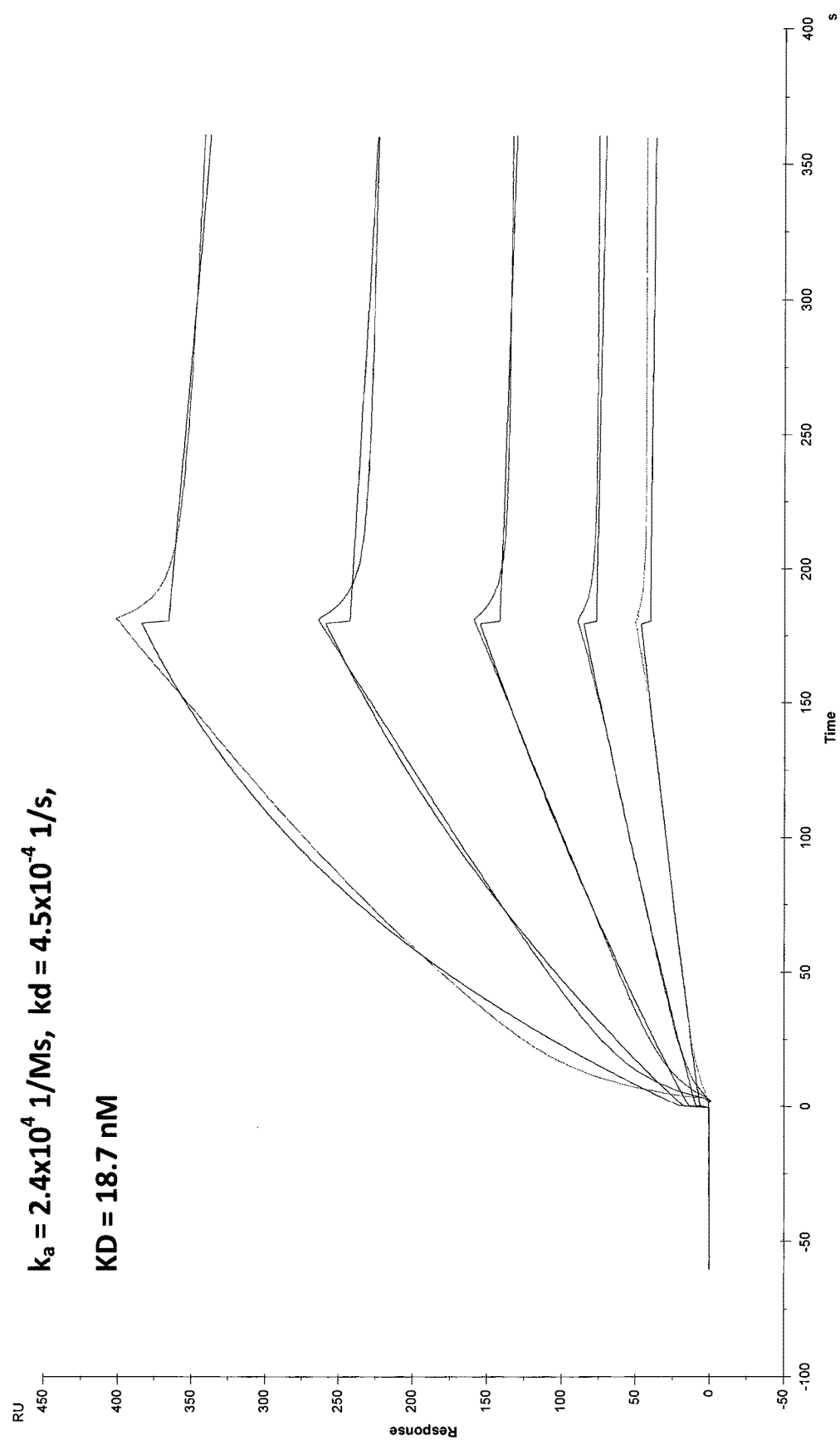
Fig. 8A: Co-binding of GMCSF + Antibody + IL6 (contd.)
$k_a = 2.4 \times 10^4$ 1/Ms, $k_d = 4.5 \times 10^{-4}$ 1/s,
$K_D = 18.7$ nM

B: Co-binding of anti-LC + Antibody + IL6

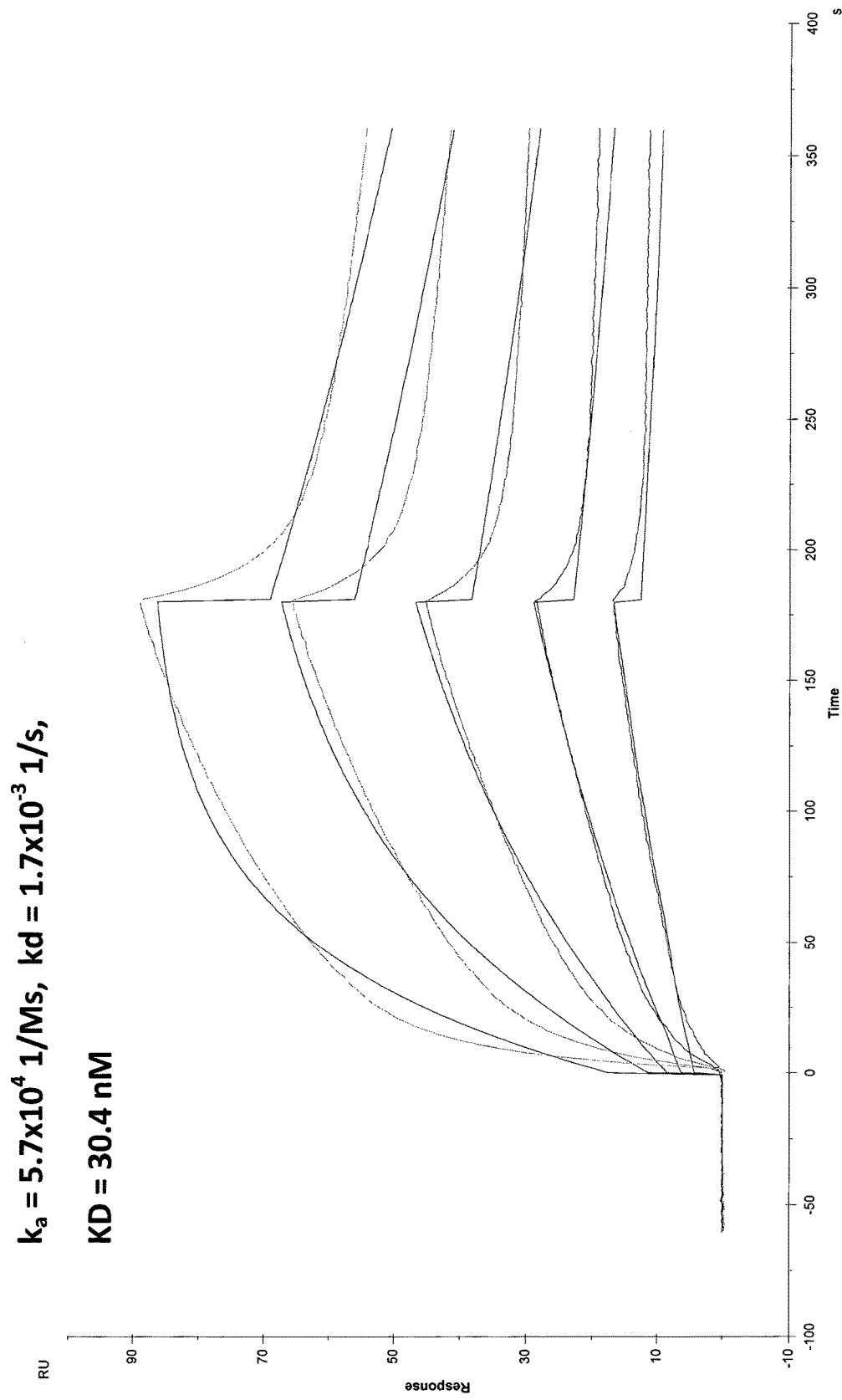

Fig. 9: Library scaffolds overview

VL domain scaffold 1 (SEQ-ID NO: 1) (= Dummy 1 Vk)

```
         10        20        30        40        50        60        70        80        90
....|....|....|....|....|....|....|....|....|....|....|....|....|....|....|....|....|....|
DTQMTQSPSSLSASVGDRVTITCRASQSISSYLAWYQQKPGKAPKLLIYAASSLYSGVPSRFSGSGSGTDFTLTISSLQPEDFATYYCQQYSSLPY
        100
....|....|....|...
TFGQGTKVEIKR
```

VH domain scaffold 1 (SEQ-ID NO: 2)(= Dummy 1 VH)

```
         10        20        30        40        50        60        70        80        90
....|....|....|....|....|....|....|....|....|....|....|....|....|....|....|...a.|....|....|...abc.|....|....|
EVQLVESGGGLVQPGGSLRLSCAASGFTFSSYAMSWIRQAPGKGLEWIGQISGSGGSTYYNDNVLGRFTISRDNSKNTLYLQMNSLRAEDTAVYYC
        100       110
....|....|....|....|....|
ARDSGYFDIWGQGTLVTVSS
```

For Libraries Lib3-L and Lib3-H:

VL domain scaffold 2 (SEQ-ID NO: 3)

DTQMTQSPSSLSASVGDRVTITCRASQSISSYLAWYQQKPGKAPKLLIYAASSLYSGVPSRFSGSGSGTDFTLTISSLQPEDFATYYCQQYSSLPY
TFGQGTK<u>L</u>EIKR

VH domain scaffold 2 (SEQ-ID NO: 4)

EVQLVESGGGLVQPGGSLRLSCAASGFTFSSYAMSWIRQAPGKGLEWIGQISGSGGSTYYNDNVLGRFTISRDNSKNTLYLQMNSLRAEDTAVYYC
ARD<u>T</u>GYFDIWGQGTLVTVSS

Fig. 9: Library scaffolds overview (contd.)

For Libraries Lib4-L and Lib4-HE_ini:
VL domain scaffold 3 (SEQ-ID NO: 5)
DTQMTQSPSSLSASVGDRVTITCRASQSISSYLAWYQQKPGKAPKLLIYDASSLQSGVPSRFSGSGSGTDFTLTISSLQPEDFATYYCQQYSSYPY
TFGQGTKLEIKR

For Libraries Lib4-LE, Lib5-L, Lib4-H, and Lib4-HE:
VL domain scaffold 4 (SEQ-ID NO: 7)
DIQMTQSPSSLSASVGDRVTITCRASQSISSYLAWYQQKPGKAPKLLIYDASSLQSGVPSRFSGSGSGTDFTLTISSLQPEDFATYYCQQYSSYPY
TFGQGTKLEIKR

For Libraries Lib4-L, Lib4-LE, Lib5-L, Lib4-H, and Lib4-HE:
VH domain scaffold 3 (SEQ-ID NO: 6)
EVQLVESGGGLVQPGGSLRLSCAASGFTFSSYAMSWVRQAPGKGLEWVGSISPSGGSTYYNDNVLGRFTISRDNSKNTLYLQMNSLRAEDTAVYYC
ARDQGYFDIWGQGTLVTVSS

Fig. 10: Diversification overview

Lib3-L

Diversified VL Domain (SEQ-ID NO: 8):
XXQMTQSPSSLSASVGDRVTITCRXXXXXXSSYLAWYQQKPGKAPKLLIYAASSLYSGVPSRFSGSGSGXXFTLTISSLQPEDFATYYCQQYSXXPYTFGQGTKLEIKR

Diversified VH Domain (SEQ-ID NO: 9):
EVQLVESGGGLVQPGGSLRLSCAASGFTFSSYAMSWIRQAPGKGLEWIGQISGSGGSTXYXXXXXGRFTISRDNSKNTLYLQMNSLRAEDTAVYYCARDTGYFDIWGQGTLVTVSS

Lib3-H

Diversified VL Domain (SEQ-ID NO: 10):
DTQMTQSPSSLSASVGDRVTITCRASQSISSYLAWYQQKPGKAPXLLIXAASXLXXXXPSRFSGSGSGTDFTLTISSLQPEDFATYYCQQYSSLPYTFGQGTKLEIKR

Diversified VH Domain (SEQ-ID NO: 11):
XXQLVESGGGLVQPGGSLRLSCAAXGFXFSXYAMSWIRQAPGKGLEWIGQISGSGGSTYYNDNVLGRFTISRDNSKXTLYLQMNSLRAEDTAVYYCARDXGXFDXWGQGTLVTVSS

Lib4-L

Diversified VL Domain (SEQ-ID NO: 12):
XXQMTQSPSSLSASVGDRVTITCXXXXXXSSYLAWYQQKPGKAPKLLIYDASSLQSGVPSRFSGSGSGTXFTLTISSLQPEDFATYYCQQYSXXPYXFGQGTKLEIKR

Diversified VH Domain (SEQ-ID NO: 13):
EVQLVESGGGLVQPGGSLRLSCAASGFTFSSYAMSWVRQAPGKGLEWVGSISPSGGSTXYYXXXXGRFTISRDNSKNTLYLQMNSLRAEDTAVYYCARDQGYFDIWGQGTLVTVSS

Fig. 10: Diversification overview (contd.)

Lib4-LE

Diversified VL Domain (SEQ-ID NO: 27):
xxQMTQSPSSLSASVGDRVTITCXXXXXXSSYLAWYQQKPGKAPKLLIYDASSLQSGVPSRFSGSGSGXXFTLTISSLQPEDFATYCQQYXXXPY XFGQGTKLEIKR

Diversified VH Domain (SEQ-ID NO: 13):
EVQLVESGGGLVQPGGSLRLSCAASGFTFSSYAMSWVRQAPGKGLEWVGSISPSGGSTXYXXXXXGRFTISRDNSKNTLYLQMNSLRAEDTAVYYC ARDQGYFDIWGQGTLVTVSS

Lib5-L

Diversified VL Domain (SEQ-ID NO: 28):
xxQXTQSPSSLSASVGDRVTITCXXXXXXSSYLAWYQQKPGKAPKLLIYDASSLQSGVPSRFSGSGSGTXFTLTISSLQPEDFATYCQQYXXXPY XFGQGTKLEIKR

Diversified VH Domain (SEQ-ID NO: 13):
EVQLVESGGGLVQPGGSLRLSCAASGFTFSSYAMSWVRQAPGKGLEWVGSISPSGGSTXYXXXXXGRFTISRDNSKNTLYLQMNSLRAEDTAVYYC ARDQGYFDIWGQGTLVTVSS

Lib4-H

Diversified VL Domain (SEQ-ID NO: 14):
DIQMTQSPSSLSASVGDRVTITCRASQSISSYLAWYQQKPGKAPKLLIXDASXXXXGVPSRFSGSGSGTDFTLTISSLQPEDFATYCQQYSSYPY TFGQGTKLEIKR

Diversified VH Domain (SEQ-ID NO: 15):
xxQLVESGGGLVQPGGSLRLSCAASXXXFSXXAMSWVRQAPGKGLEWVGSISPSGGSTYYNDNVLGRFTISRDNSKNTLYLQMNSLRAEDTAVYYC AXDXGXFDXWGQGTLVTVSS

Fig. 10: Diversification overview (contd.)

Lib4-HE_ini

Diversified VL Domain (SEQ-ID NO: 16):
DIQMTQSPSSLSASVGDRVTITCRASQSISSYLAWYQQKPGKAPKLLIXDASXXXXXXPXRFSGSGSGTDFTLTISSLQPEDFATYYCQQYSSYPY
TFGQGTKLEIKR

Diversified VH Domain (SEQ-ID NO: 17):
XXQLVESGGGLVQPGGSLRLSCAAXXXXXFSXXAMSWVRQAPGKGLEWVGSISPSGGSTYYNDVLGRFTISRDNSKNTLYLQMNSLRAEDTAVYYC
AXDXGXFDXWGQGTLVTVSS

Lib4-HE

Diversified VL Domain (SEQ-ID NO: 29):
DIQMTQSPSSLSASVGDRVTITCRASQSISSYLAWYQQKPGKAPKLLIXDASXXXXXXPXRFSGSGSGTDFTLTISSLQPEDFATYYCQQYSSYPY
TFGQGTKLEIKR

Diversified VH Domain (SEQ-ID NO: 17):
XXQLVESGGGLVQPGGSLRLSCAAXXXXXFSXXAMSWVRQAPGKGLEWVGSISPSGGSTYYNDVLGRFTISRDNSKNTLYLQMNSLRAEDTAVYYC
AXDXGXFDXWGQGTLVTVSS

SEQUENCE LISTING

```
<160> NUMBER OF SEQ ID NOS: 49

<210> SEQ ID NO 1
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 1

Asp Thr Gln Met Thr Gln Ser Pro Ser Ser Leu Ser Ala Ser Val Gly
```

```
                1               5                  10                 15
            Asp Arg Val Thr Ile Thr Cys Arg Ala Ser Gln Ser Ile Ser Ser Tyr
                            20                  25                 30

Leu Ala Trp Tyr Gln Gln Lys Pro Gly Lys Ala Pro Lys Leu Leu Ile
                        35                  40                  45

Tyr Ala Ala Ser Ser Leu Tyr Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Phe Ala Thr Tyr Tyr Cys Gln Gln Tyr Ser Ser Leu Pro Tyr
                            85                  90                  95

Thr Phe Gly Gln Gly Thr Lys Val Glu Ile Lys Arg
                        100                 105

<210> SEQ ID NO 2
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 2

Glu Val Gln Leu Val Glu Ser Gly Gly Gly Leu Val Gln Pro Gly Gly
            1               5                   10                  15

Ser Leu Arg Leu Ser Cys Ala Ala Ser Gly Phe Thr Phe Ser Ser Tyr
                            20                  25                  30

Ala Met Ser Trp Ile Arg Gln Ala Pro Gly Lys Gly Leu Glu Trp Ile
                        35                  40                  45

Gly Gln Ile Ser Gly Ser Gly Gly Ser Thr Tyr Tyr Asn Asp Asn Val
                    50                  55                  60

Leu Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Arg Asp Ser Gly Tyr Phe Asp Ile Trp Gly Gln Gly Thr Leu Val
                        100                 105                 110

Thr Val Ser Ser
                    115

<210> SEQ ID NO 3
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 3

Asp Thr Gln Met Thr Gln Ser Pro Ser Ser Leu Ser Ala Ser Val Gly
            1               5                   10                  15

Asp Arg Val Thr Ile Thr Cys Arg Ala Ser Gln Ser Ile Ser Ser Tyr
                            20                  25                  30

Leu Ala Trp Tyr Gln Gln Lys Pro Gly Lys Ala Pro Lys Leu Leu Ile
                        35                  40                  45

Tyr Ala Ala Ser Ser Leu Tyr Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80
```

Glu Asp Phe Ala Thr Tyr Tyr Cys Gln Gln Tyr Ser Ser Leu Pro Tyr
                85                  90                  95

Thr Phe Gly Gln Gly Thr Lys Leu Glu Ile Lys Arg
            100                 105

<210> SEQ ID NO 4
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Gly Ser Thr Tyr Tyr Asn Asp Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Tyr Phe Asp Ile Trp Gly Gln Gly Thr Leu Val
            100                 105                 110

Thr Val Ser Ser
        115

<210> SEQ ID NO 5
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 5

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg
            100                 105

<210> SEQ ID NO 6
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 6

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Gly Ser Ile Ser Pro Ser Gly Gly Ser Thr Tyr Tyr Asn Asp Asn Val
50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Phe Asp Ile Trp Gly Gln Gly Thr Leu Val
            100                 105                 110

Thr Val Ser Ser
        115

<210> SEQ ID NO 7
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg
            100                 105

<210> SEQ ID NO 8
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in position 1: residue diversified or absent;
      X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (25)..(29)
<223> OTHER INFORMATION: Xaa can be any naturally occurring amino acid
<220> FEATURE:
<221> NAME/KEY: misc_feature
<222> LOCATION: (69)..(70)

```
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid

<400> SEQUENCE: 8

Xaa Xaa Gln Met Thr Gln Ser Pro Ser Ser Leu Ser Ala Ser Val Gly
1               5                   10                  15

Asp Arg Val Thr Ile Thr Cys Arg Xaa Xaa Xaa Xaa Ser Ser Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Tyr Ser Gly Val Pro Ser Arg Phe Ser Gly
50                  55                  60

Ser Gly Ser Gly Xaa Xaa Phe Thr Leu Thr Ile Ser Ser Leu Gln Pro
65                  70                  75                  80

Glu Asp Phe Ala Thr Tyr Tyr Cys Gln Gln Tyr Ser Xaa Xaa Pro Tyr
                85                  90                  95

Thr Phe Gly Gln Gly Thr Lys Leu Glu Ile Lys Arg
            100                 105

<210> SEQ ID NO 9
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(65)
<223> OTHER INFORMATION: Xaa can be any naturally occurring amino acid

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Ile
            35                  40                  45

Gly Gln Ile Ser Gly Ser Gly Gly Ser Thr Xaa Tyr Xaa Xaa Xaa Xaa
50                  55                  60

Xaa Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Tyr Phe Asp Ile Trp Gly Gln Gly Thr Leu Val
            100                 105                 110

Thr Val Ser Ser
        115

<210> SEQ ID NO 10
<211> LENGTH: 108
<212> TYPE: PRT
<213> ORGANISM: Artificial sequence
```

```
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(58)
<223> OTHER INFORMATION: Xaa can be any naturally occurring amino acid

<400> SEQUENCE: 10

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Xaa Leu Leu Ile
        35                  40                  45

Xaa Ala Ala Ser Xaa Leu Xaa Xaa Xaa Xaa Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Leu Pro Tyr
                85                  90                  95

Thr Phe Gly Gln Gly Thr Lys Leu Glu Ile Lys Arg
            100                 105

<210> SEQ ID NO 11
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in position 1: residue diversified or absent;
      X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (100)..(100)
```

<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 11

Xaa Xaa Gln Leu Val Glu Ser Gly Gly Gly Leu Val Gln Pro Gly Gly
  1               5                  10                  15

Ser Leu Arg Leu Ser Cys Ala Ala Xaa Gly Phe Xaa Phe Ser Xaa Tyr
             20                  25                  30

Ala Met Ser Trp Ile Arg Gln Ala Pro Gly Lys Gly Leu Glu Trp Ile
         35                  40                  45

Gly Gln Ile Ser Gly Ser Gly Gly Ser Thr Tyr Tyr Asn Asp Asn Val
     50                  55                  60

Leu Gly Arg Phe Thr Ile Ser Arg Asp Asn Ser Lys Xaa Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Xaa Gly Xaa Phe Asp Xaa Trp Gly Gln Gly Thr Leu Val
            100                 105                 110

Thr Val Ser Ser
        115

<210> SEQ ID NO 12
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in position 1: residue diversified or absent;
      X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (24)..(29)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 12

Xaa Xaa Gln Met Thr Gln Ser Pro Ser Ser Leu Ser Ala Ser Val Gly
  1               5                  10                  15

Asp Arg Val Thr Ile Thr Cys Xaa Xaa Xaa Xaa Xaa Xaa Ser Ser Tyr
             20                  25                  30

Leu Ala Trp Tyr Gln Gln Lys Pro Gly Lys Ala Pro Lys Leu Leu Ile
         35                  40                  45

```
Tyr Asp Ala Ser Ser Leu Gln Ser Gly Val Pro Ser Arg Phe Ser Gly
    50                  55                  60

Ser Gly Ser Gly Thr Xaa Phe Thr Leu Thr Ile Ser Ser Leu Gln Pro
65                  70                  75                  80

Glu Asp Phe Ala Thr Tyr Tyr Cys Gln Gln Tyr Ser Xaa Xaa Pro Tyr
                85                  90                  95

Xaa Phe Gly Gln Gly Thr Lys Leu Glu Ile Lys Arg
            100                 105
```

```
<210> SEQ ID NO 13
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(65)
<223> OTHER INFORMATION: Xaa can be any naturally occurring amino acid

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ser Ile Ser Pro Ser Gly Gly Ser Thr Xaa Tyr Xaa Xaa Xaa Xaa
    50                  55                  60

Xaa Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Phe Asp Ile Trp Gly Gln Gly Thr Leu Val
            100                 105                 110

Thr Val Ser Ser
        115
```

```
<210> SEQ ID NO 14
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(56)
<223> OTHER INFORMATION: Xaa can be any naturally occurring amino acid

<400> SEQUENCE: 14

Asp Ile Gln Met Thr Gln Ser Pro Ser Ser Leu Ser Ala Ser Val Gly
```

```
1               5                   10                  15
Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
            35                  40                  45

Xaa Asp Ala Ser Xaa Xaa Xaa Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg
            100                 105
```

<210> SEQ ID NO 15
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in positions 1:and 27: residues diversified
    or absent; X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 15

```
Xaa Xaa Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Phe Ser Xaa Xaa
            20                  25                  30

Ala Met Ser Trp Val Arg Gln Ala Pro Gly Lys Gly Leu Glu Trp Val
            35                  40                  45

Gly Ser Ile Ser Pro Ser Gly Ser Thr Tyr Tyr Asn Asp Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

Ala Xaa Asp Xaa Gly Xaa Phe Asp Xaa Trp Gly Gln Gly Thr Leu Val
            100                 105                 110

Thr Val Ser Ser
        115

<210> SEQ ID NO 16
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 16

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Xaa Asp Ala Ser Xaa Xaa Xaa Xaa Xaa Pro Xaa Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg
            100                 105

<210> SEQ ID NO 17
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in positions 1:and 27: residues diversified
      or absent; X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (98)..(98)

<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 17

Xaa Xaa Gln Leu Val Glu Ser Gly Gly Gly Leu Val Gln Pro Gly Gly
1               5                   10                  15

Ser Leu Arg Leu Ser Cys Ala Ala Xaa Xaa Xaa Phe Ser Xaa Xaa
            20                  25                  30

Ala Met Ser Trp Val Arg Gln Ala Pro Gly Lys Gly Leu Glu Trp Val
        35                  40                  45

Gly Ser Ile Ser Pro Ser Gly Gly Ser Thr Tyr Tyr Asn Asp Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Xaa Asp Xaa Gly Xaa Phe Asp Xaa Trp Gly Gln Gly Thr Leu Val
            100                 105                 110

Thr Val Ser Ser
        115

<210> SEQ ID NO 18
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (25)..(29)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 18

Xaa Xaa Gln Met Thr Gln Ser Pro Ser Ser Leu Ser Ala Ser Val Gly
1               5                   10                  15

Asp Arg Val Thr Ile Thr Cys Arg Xaa Xaa Xaa Xaa Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Tyr Ser Gly Val Pro Ser Arg Phe Ser Gly

```
                 50                  55                  60

Ser Gly Ser Gly Xaa Xaa Phe Thr Leu Thr Ile Ser Ser Leu Gln Pro
 65                  70                  75                  80

Glu Asp Phe Ala Thr Tyr Tyr Cys Gln Gln Tyr Ser Xaa Leu Pro Tyr
                 85                  90                  95

Thr Phe Gly Gln Gly Thr Lys Val Glu Ile Lys Arg
            100                 105

<210> SEQ ID NO 19
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (25)..(29)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid

<400> SEQUENCE: 19

Xaa Xaa Xaa Met Thr Gln Ser Pro Ser Ser Leu Ser Ala Ser Val Gly
 1               5                  10                  15

Asp Arg Val Thr Ile Thr Cys Arg Xaa Xaa Xaa Xaa Xaa Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Tyr Ser Gly Val Pro Ser Arg Phe Ser Gly
 50                  55                  60

Ser Gly Ser Gly Xaa Xaa Phe Thr Leu Thr Ile Ser Ser Leu Gln Pro
 65                  70                  75                  80

Glu Asp Phe Ala Thr Tyr Tyr Cys Gln Gln Tyr Ser Xaa Xaa Pro Tyr
                 85                  90                  95

Thr Phe Gly Gln Gly Thr Lys Val Glu Ile Lys Arg
            100                 105

<210> SEQ ID NO 20
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(65)
<223> OTHER INFORMATION: Xaa can be any naturally occurring amino acid
```

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Ser Thr Xaa Tyr Xaa Xaa Xaa Xaa
    50                  55                  60

Xaa Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Phe Asp Ile Trp Gly Gln Gly Thr Leu Val
            100                 105                 110

Thr Val Ser Ser
        115

<210> SEQ ID NO 21
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(65)
<223> OTHER INFORMATION: Xaa can be any naturally occurring amino acid

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Xaa Trp Ile
        35                  40                  45

Gly Gln Ile Ser Gly Ser Gly Ser Thr Xaa Tyr Xaa Xaa Xaa Xaa
    50                  55                  60

Xaa Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Phe Asp Ile Trp Gly Gln Gly Thr Leu Val
            100                 105                 110

Thr Val Ser Ser
        115

<210> SEQ ID NO 22
<211> LENGTH: 108

```
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(58)
<223> OTHER INFORMATION: Xaa can be any naturally occurring amino acid

<400> SEQUENCE: 22

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Xaa Leu Leu Ile
        35                  40                  45

Xaa Ala Ala Ser Xaa Leu Xaa Xaa Xaa Xaa Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Leu Pro Tyr
                85                  90                  95

Thr Phe Gly Gln Gly Thr Lys Val Glu Ile Lys Arg
            100                 105

<210> SEQ ID NO 23
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(58)
<223> OTHER INFORMATION: Xaa can be any naturally occurring amino acid

<400> SEQUENCE: 23

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
```

```
                35                  40                  45
Xaa Ala Ala Ser Xaa Leu Xaa Xaa Xaa Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Leu Pro Tyr
                85                  90                  95

Thr Phe Gly Gln Gly Thr Lys Val Glu Ile Lys Arg
            100                 105

<210> SEQ ID NO 24
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 24

Xaa Xaa Gln Leu Val Glu Ser Gly Gly Gly Leu Val Gln Pro Gly Gly
 1               5                  10                  15

Ser Leu Arg Leu Ser Cys Ala Ala Xaa Gly Phe Xaa Phe Ser Xaa Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Gly Ser Thr Tyr Tyr Asn Asp Asn Val
    50                  55                  60

Leu Gly Arg Phe Thr Ile Ser Arg Asp Asn Ser Lys Xaa Thr Leu Tyr
 65                  70                  75                  80

Leu Gln Met Asn Ser Leu Arg Ala Glu Asp Thr Ala Val Tyr Tyr Cys
                85                  90                  95

Ala Xaa Asp Ser Gly Tyr Phe Asp Xaa Trp Gly Gln Gly Thr Leu Val
            100                 105                 110

Thr Val Ser Ser
        115
```

<210> SEQ ID NO 25
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 25

Xaa Xaa Xaa Leu Val Glu Ser Gly Gly Gly Leu Val Gln Pro Gly Gly
1               5                   10                  15

Ser Leu Arg Leu Ser Cys Ala Ala Xaa Gly Xaa Xaa Xaa Ser Xaa Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Gly Ser Thr Tyr Tyr Asn Asp Asn Val
    50                  55                  60

Leu Gly Arg Phe Thr Ile Ser Arg Asp Asn Ser Lys Xaa Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Ser Gly Tyr Phe Asp Xaa Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid -continued

```
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 26

Xaa Xaa Gln Leu Val Glu Ser Gly Gly Gly Leu Val Gln Pro Gly Gly
 1               5                   10                  15

Ser Leu Arg Leu Ser Cys Ala Ala Ser Gly Xaa Xaa Xaa Ser Xaa Xaa
             20                  25                  30

Ala Met Ser Trp Ile Arg Gln Ala Pro Gly Lys Gly Leu Glu Trp Ile
         35                  40                  45

Gly Gln Ile Ser Gly Ser Gly Ser Thr Tyr Tyr Asn Asp Asn Val
     50                  55                  60

Leu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Xaa Gly Xaa Phe Asp Xaa Trp Gly Gln Gly Thr Leu Val
            100                 105                 110

Thr Val Ser Ser
        115

<210> SEQ ID NO 27
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in position 1: residue diversified or absent;
      X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (24)..(29)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (92)..(94)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 27

Xaa Xaa Gln Met Thr Gln Ser Pro Ser Ser Leu Ser Ala Ser Val Gly
 1               5                   10                  15
```

Asp Arg Val Thr Ile Thr Cys Xaa Xaa Xaa Xaa Xaa Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Xaa Xaa Phe Thr Leu Thr Ile Ser Ser Leu Gln Pro
65                  70                  75                  80

Glu Asp Phe Ala Thr Tyr Tyr Cys Gln Gln Tyr Xaa Xaa Xaa Pro Tyr
                85                  90                  95

Xaa Phe Gly Gln Gly Thr Lys Leu Glu Ile Lys Arg
            100                 105

<210> SEQ ID NO 28
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X in position 1: residue diversified or absent;
      X in other positions: diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(29)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (92)..(94)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 28

Xaa Xaa Gln Xaa Thr Gln Ser Pro Ser Ser Leu Ser Ala Ser Val Gly
1               5                   10                  15

Asp Arg Val Thr Ile Thr Cys Xaa Xaa Xaa Xaa Xaa Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Thr Xaa Phe Thr Leu Thr Ile Ser Ser Leu Gln Pro
65                  70                  75                  80

Glu Asp Phe Ala Thr Tyr Tyr Cys Gln Gln Tyr Xaa Xaa Xaa Pro Tyr
                85                  90                  95

Xaa Phe Gly Gln Gly Thr Lys Leu Glu Ile Lys Arg
            100                 105

-continued

```
<210> SEQ ID NO 29
<211> LENGTH: 108
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Xaa Asp Ala Ser Xaa Xaa Xaa Xaa Xaa Pro Xaa Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg
            100                 105

<210> SEQ ID NO 30
<211> LENGTH: 110
<212> TYPE: PRT
<213> ORGANISM: Artificial sequence
<220> FEATURE:
<223> OTHER INFORMATION: artificial antibody variable domain

<400> SEQUENCE: 30

Ser Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 31
<211> LENGTH: 110
```

```
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (25)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (94)..(97)
<223> OTHER INFORMATION: Xaa can be any naturally occurring amino acid

<400> SEQUENCE: 31

Xaa Xaa Val Leu Thr Gln Pro Pro Ser Val Ser Gly Ala Pro Gly Gln
1               5                   10                  15

Arg Val Thr Ile Ser Cys Ser Gly Xaa Xaa Xaa Asn Ile Gly Xaa Asn
            20                  25                  30

Thr Val Ser Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Gly Xaa Ser Ala Ser Leu Ala Ile Thr Gly Leu Gln
65                  70                  75                  80

Ser Glu Asp Glu Ala Asp Tyr Tyr Cys Ala Ala Trp Asp Xaa Xaa Xaa
                85                  90                  95

Xaa Gly Tyr Val Phe Gly Thr Gly Thr Lys Val Thr Val Leu
            100                 105                 110

<210> SEQ ID NO 32
<211> LENGTH: 117
<212> TYPE: PRT
<213> ORGANISM: Artificial sequence
<220> FEATURE:
<223> OTHER INFORMATION: artificial antibody variable domain

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Gly Thr Ile Ser Gly Ser Gly Gly Ser Thr Tyr Tyr Asn Asp Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Thr Ser Ser Gly Tyr Phe Asp Tyr Trp Gly Gln Gly Thr Leu
            100                 105                 110

Val Thr Val Ser Ser
        115

<210> SEQ ID NO 33
<211> LENGTH: 117
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(65)
<223> OTHER INFORMATION: Xaa can be any naturally occurring amino acid

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Gly Thr Ile Ser Gly Ser Gly Gly Ser Thr Xaa Tyr Xaa Xaa Xaa Xaa
    50                  55                  60

Xaa Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ser Ser Gly Tyr Phe Asp Tyr Trp Gly Gln Gly Thr Leu
            100                 105                 110

Val Thr Val Ser Ser
        115

<210> SEQ ID NO 34
<211> LENGTH: 110
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(59)
<223> OTHER INFORMATION: Xaa can be any naturally occurring amino acid

<400> SEQUENCE: 34

Ser Ser Val Leu Thr Gln Pro Pro Ser Val Ser Gly Ala Pro Gly Gln
1               5                   10                  15

```
Arg Val Thr Ile Ser Cys Ser Gly Ser Ser Asn Ile Gly Ser Asn
             20                  25                  30

Thr Val Ser Trp Tyr Gln Gln Leu Pro Gly Thr Ala Pro Lys Leu Leu
         35                  40                  45

Ile Xaa Gly Asn Asn Xaa Arg Xaa Xaa Xaa Xaa Pro Asp Arg Phe Ser
 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Ala Ala Trp Asp Asp Ser Leu
             85                  90                  95

Asn Gly Tyr Val Phe Gly Thr Gly Thr Lys Val Thr Val Leu
            100                 105                 110

<210> SEQ ID NO 35
<211> LENGTH: 117
<212> TYPE: PRT
<213> ORGANISM: Artificial sequence
<220> FEATURE:
<223> OTHER INFORMATION: artificial antibody variable domain
<220> FEATURE:
<221> NAME/KEY: MISC_FEATURE
<223> OTHER INFORMATION: X diversified residues
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(101)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid

<400> SEQUENCE: 35

Xaa Xaa Gln Leu Val Glu Ser Gly Gly Gly Leu Val Gln Pro Gly Gly
 1               5                  10                  15

Ser Leu Arg Leu Ser Cys Ala Ala Ser Gly Xaa Xaa Xaa Ser Xaa Xaa
             20                  25                  30

Tyr Met Ser Trp Val Arg Gln Ala Pro Gly Lys Gly Leu Glu Trp Val
         35                  40                  45

Gly Thr Ile Ser Gly Ser Gly Gly Ser Thr Tyr Tyr Asn Asp Asn Val
 50                  55                  60

Leu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Xaa Thr Xaa Xaa Gly Xaa Phe Asp Xaa Trp Gly Gln Gly Thr Leu
            100                 105                 110
```

Val Thr Val Ser Ser
        115

<210> SEQ ID NO 36
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 36

Gly Ile Gln Met Thr Gln Ser Pro Ser Ser Leu Ser Ala Ser Val Gly
1               5                   10                  15

Asp Arg Val Thr Ile Thr Cys Arg Ala Arg Trp Tyr Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Tyr Ser Gly Val Pro Ser Arg Phe Ser Gly
    50                  55                  60

Ser Gly Ser Gly Lys Asp Phe Thr Leu Thr Ile Ser Ser Leu Gln Pro
65                  70                  75                  80

Glu Asp Phe Ala Thr Tyr Tyr Cys Gln Gln Tyr Ser Glu Leu Pro Tyr
                85                  90                  95

Thr Phe Gly Gln Gly Thr Lys Val Glu Ile Lys Arg
            100                 105

<210> SEQ ID NO 37
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 37

Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Phe Ala Ala Ser Arg Leu Ile Leu Asn Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Leu Pro Tyr
                85                  90                  95

Thr Phe Gly Gln Gly Thr Lys Val Glu Ile Lys Arg
            100                 105

<210> SEQ ID NO 38
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 38

Gly Ile Gln Met Thr Gln Ser Pro Ser Ser Leu Ser Ala Ser Val Gly
1               5                   10                  15

Asp Arg Val Thr Ile Thr Cys Arg Ala Arg Trp Tyr Ile Ser Ser Tyr
            20                  25                  30

Leu Ala Trp Tyr Gln Gln Lys Pro Gly Lys Ala Pro Lys Leu Leu Ile
        35                  40                  45

Phe Ala Ala Ser Arg Leu Ile Leu Asn Val Pro Ser Arg Phe Ser Gly
    50                  55                  60

Ser Gly Ser Gly Lys Asp Phe Thr Leu Thr Ile Ser Ser Leu Gln Pro
65                  70                  75                  80

Glu Asp Phe Ala Thr Tyr Tyr Cys Gln Gln Tyr Ser Glu Leu Pro Tyr
                85                  90                  95

Thr Phe Gly Gln Gly Thr Lys Val Glu Ile Lys Arg
            100                 105

<210> SEQ ID NO 39
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Ser Thr Trp Tyr Asn His Asp Ile
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Phe Asp Ile Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 40

Trp Val Gln Leu Val Glu Ser Gly Gly Gly Leu Val Gln Pro Gly Gly
1               5                   10                  15

Ser Leu Arg Leu Ser Cys Ala Arg Gly Phe Pro Phe Ser His Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Ser Thr Tyr Tyr Asn Asp Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Phe Asp Trp Trp Gly Gln Gly Thr Leu Val
            100                 105                 110

Thr Val Ser Ser
        115

<210> SEQ ID NO 41
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 41

Trp Val Gln Leu Val Glu Ser Gly Gly Gly Leu Val Gln Pro Gly Gly
1               5                   10                  15

Ser Leu Arg Leu Ser Cys Ala Ala Arg Gly Phe Pro Phe Ser His Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Gly Ser Thr Trp Tyr Asn His Asp Ile
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Phe Asp Trp Trp Gly Gln Gly Thr Leu Val
            100                 105                 110

Thr Val Ser Ser
        115

<210> SEQ ID NO 42
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 42

Asn Ile Gln Lys Thr Gln Ser Pro Ser Ser Leu Ser Ala Ser Val Gly
1               5                   10                  15

Asp Arg Val Thr Ile Thr Cys Arg Ala Leu Trp His Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Leu Pro Tyr
                85                  90                  95

Thr Phe Gly Gln Gly Thr Lys Val Glu Ile Lys Arg
            100                 105

<210> SEQ ID NO 43
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 43

```
Asp Thr Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser His Leu His Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Leu Pro Tyr
                85                  90                  95

Thr Phe Gly Gln Gly Thr Lys Val Glu Ile Lys Arg
            100                 105
```

<210> SEQ ID NO 44
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 44

```
Asn Ile Gln Lys Thr Gln Ser Pro Ser Ser Leu Ser Ala Ser Val Gly
1               5                   10                  15

Asp Arg Val Thr Ile Thr Cys Arg Ala Leu Trp His Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser His Leu His Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Leu Pro Tyr
                85                  90                  95

Thr Phe Gly Gln Gly Thr Lys Val Glu Ile Lys Arg
            100                 105
```

<210> SEQ ID NO 45
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Gly Ser Thr Val Tyr Asn Tyr Asn Val
    50                  55                  60

Leu Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Arg Asp Ser Gly Tyr Phe Asp Ile Trp Gly Gln Gly Thr Leu Val
            100                 105                 110

Thr Val Ser Ser
        115

<210> SEQ ID NO 46
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 46

Tyr Tyr Gln Leu Val Glu Ser Gly Gly Gly Leu Val Gln Pro Gly Gly
1               5                   10                  15

Ser Leu Arg Leu Ser Cys Ala Ala Asp Gly Phe Leu Phe Ser Gly Tyr
            20                  25                  30

Ala Met Ser Trp Ile Arg Gln Ala Pro Gly Lys Gly Leu Glu Trp Ile
            35                  40                  45

Gly Gln Ile Ser Gly Ser Gly Gly Ser Thr Tyr Tyr Asn Asp Asn Val
        50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Tyr Phe Asp His Trp Gly Gln Gly Thr Leu Val
            100                 105                 110

Thr Val Ser Ser
        115

<210> SEQ ID NO 47
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 47

Tyr Tyr Gln Leu Val Glu Ser Gly Gly Gly Leu Val Gln Pro Gly Gly
1               5                   10                  15

Ser Leu Arg Leu Ser Cys Ala Ala Asp Gly Phe Leu Phe Ser Gly Tyr
            20                  25                  30

Ala Met Ser Trp Ile Arg Gln Ala Pro Gly Lys Gly Leu Glu Trp Ile
            35                  40                  45

Gly Gln Ile Ser Gly Ser Gly Gly Ser Thr Val Tyr Asn Tyr Asn Val
        50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Tyr Phe Asp His Trp Gly Gln Gly Thr Leu Val
            100                 105                 110

Thr Val Ser Ser
        115

```
<210> SEQ ID NO 48
<211> LENGTH: 108
<212> TYPE: PRT
<213> ORGANISM: Artificial sequence
<220> FEATURE:
<223> OTHER INFORMATION: artificial antibody variable domain

<400> SEQUENCE: 48

Ala Thr Gln Arg Thr Gln Ser Pro Ser Ser Leu Ser Ala Ser Val Gly
1               5                   10                  15

Asp Arg Val Thr Ile Thr Cys Arg Ala Leu Trp His Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Trp Leu Tyr Trp Asp Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Gly Leu Pro Tyr
                85                  90                  95

Thr Phe Gly Gln Gly Thr Lys Val Glu Ile Lys Arg
            100                 105

<210> SEQ ID NO 49
<211> LENGTH: 116
<212> TYPE: PRT
<213> ORGANISM: Artificial sequence
<220> FEATURE:
<223> OTHER INFORMATION: artificial antibody variable domain

<400> SEQUENCE: 49

Trp Val Gln Leu Val Glu Ser Gly Gly Gly Leu Val Gln Pro Gly Gly
1               5                   10                  15

Ser Leu Arg Leu Ser Cys Ala Ala Lys Gly Ala Leu Phe Ser Thr Tyr
            20                  25                  30

Ala Met Ser Trp Ile Arg Gln Ala Pro Gly Lys Gly Leu Glu Trp Ile
        35                  40                  45

Gly Gln Ile Ser Gly Ser Gly Ser Thr Val Tyr Asn Tyr Asn Val
    50                  55                  60

Leu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Tyr Phe Asp Ile Trp Gly Gln Gly Thr Leu Val
            100                 105                 110

Thr Val Ser Ser
            115
```

DUAL TARGETING

CROSS REFERENCE TO RELATED APPLICATIONS

The present invention is filed under 35 U.S.C. § 371 as the U.S. national phase of International Application No. PCT/EP2013/003688, filed Dec. 5, 2013, which designated the U.S. and claims the benefit of priority to European Patent Application No. 12008154.2, filed Dec. 5, 2012, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Jun. 3, 2015, is named WRPATDUT5_SeqListing.txt and is 66kilobytes in size.

FIELD OF THE INVENTION

The present invention relates to antibody-based dual targeting molecules, and to methods for generating such dual targeting molecules, including library-based approaches.

BACKGROUND OF THE INVENTION

This invention relates to a novel design for bispecific antibodies or functional fragments thereof.

In the literature various approaches to generating bispecific antibody molecules have been reported. These approaches can be divided into two categories: 1) generating bispecific antibody formats in which the two paratopes recognizing two targets or two epitopes both lie within one heterodimeric antibody variable region formed by one complementary VH-VL pair and both comprise CDR residues belonging to this complementary VH-VL pair, and 2) generating other bispecific antibody formats in which the two paratopes recognizing two targets or epitopes do not both lie within one heterodimeric antibody variable region formed by one complementary VH-VL pair and do not both comprise CDR residues belonging to the same complementary VH-VL pair.

Within the first category of approaches, only two methods of predictably engineering bi-specific antibody molecules have been described in the literature, and these will be discussed in detail below in Sections [0014] to [0015]. However, to put this work into context, the second category of approaches will be summarized first.

This second category of approaches (in which the two paratopes recognizing two targets or epitopes do not both lie within one heterodimeric antibody variable region formed by one complementary VH-VL pair and do not both comprise CDR residues belonging to the same complementary VH-VL pair) constitutes a very large body of work by various previous workers, and numerous diverse examples of such bi-specific antibodies have been described.

In a first group of examples belonging to the second category of approaches, two or more antibody fragments (including Fab fragments, single chain Fvs, or single domain antibodies) of different specificities are combined by chemical linkage or by genetic fusion via one or more peptide linkers. Published bi-specific antibody formats in this group of examples include the following:

a. Diabodies (Perisic et al., Structure. 1994 Dec. 15; 2(12): 1217-26; Kontermann, Acta Pharmacol Sin. 2005 Jan. 26(1): 1-9; Kontermann, Curr Opin Mol Ther. 2010 Apr. 12 (2): 176-83.)
b. TandAbs etc. (Cochlovius et al., Cancer Res. 2000 Aug. 15; 60(16):4336-41.)
c. Single domains specific to different targets genetically fused by peptide linkers (e.g. Domantis: WO2008/096158; Ablynx: WO2007/112940)
d. Others (for reviews, see: Enever et al., Curr Opin Biotechnol. 20 Aug. 2009 (4): 405-11. Epub 24 Aug. 2009; Carter, Nat. Rev. Immunol. 6, 343 (2006); P. Kufer et al., Trends Biotechnol. 22, 238 (2004)).

To improve their potential usability in medical applications, the in vivo serum half-life of the above bi-specific antibody formats can be extended using various technologies, including the following:

a. Addition of serum albumin or a serum albumin binding entity
b. PEGylation
c. Addition of a protein polymer by genetic fusion, such as HAPylation (Schlapschy et al., Protein Eng Des Sel. 2007 Jun.; 20 (6): 273-84. Epub 2007Jun. 26 ) or XTEN (Schellenberger, Nat. Biotechnology 12 (2009) 1186).

In this group of examples, the bispecific antibodies comprised of antibody fragments lack an Fc region and therefore generally do not show the natural binding to the neonatal Fc receptor FcRn, do not exhibit the natural effector functions (ADCC and CDC, ref.) of full IgG antibodies, and can usually not be purified via superantigen-derived affinity resins, such as protein A resins specific for the Fc region, in an identical manner to IgG antibodies. These consequences of lack of an Fc region can limit the achievable serum half-life, the feasible applications as active drug ingredients and the economic manufacturing of such bispecific antibodies.

In a second group of examples belonging to the second category of approaches, bispecific antibodies comprise an IgG-like molecule and one or several additional appended binding domains or entities. Such antibodies include IgG-scFv fusion proteins in which a single chain Fv has been fused to one of the termini of the heavy chains or light chains (University of California, Biogen Idec, CAT/MedImmune), and dual variable domain (dvd-IgG) molecules in which an additional VH domain and a linker are fused to the N-terminus of the heavy chain and an additional VL domain and a linker are fused to the N-terminus of the light chain (Abbott). In general these approaches suffer from disadvantages in terms of manufacturing, accessibility, and stability of the constructs.

In a third group of examples belonging to the second category of approaches, bispecific antibodies comprise IgG-like antibodies that have been generated or modified in such a way that they exhibit two specificities without the addition of a further binding domain or entity. Such antibodies include IgG molecules in which the naturally homodimeric CH3 domain has been modified to become heterodimeric, e.g. using an engineered protuberation (Ridgway et al., Protein Eng. 1996 Jul.; 9(7):617-21), using strand exchange (Davis et al., Protein Eng Des Sel. 2010 Apr.; 23 (4):195-202. Epub 2010 Feb. 4), or using engineered opposite charges (Novo Nordisk), thereby potentially enabling the two halves of the IgG-like molecule to bind two different targets through the binding entities added to the Fc region, usually N-terminal Fab regions. Antibodies in this third group of examples also include IgG molecules in which some structural loops not naturally involved in antigen contacts are modified to bind a further target in addition to one bound naturally through variable region CDR loops, for example by point mutations in the Fc region (e.g. Xencor Fcs binding to FcgR11b) or by diversification of structural loops (e.g. f-star Mab2 with diversified CH3 domain). These approaches suffer from disadvantages in terms of stability, manufacturing, valency, and limited affinity/applications.

In contrast to all of the above examples of bi-specific antibodies in the second category, bi-specific antibodies in the first category have two paratopes specific for two targets which both comprise CDR residues located within the same heterodimeric VH-VL antibody variable region. Only four types of antibody molecules attributable to this first category have been described in the art. Of these four types, the first type of antibody is not truly bi-specific as it cannot specifically recognize two unrelated targets; the second type of antibody occurs naturally but it is not known whether it can be predictably engineered as no example of such work is published; and only the third and fourth types of antibody can be engineered with specificity towards two unrelated targets according to publications. The four types of antibody molecules attributable to the first category are the following:

Cross-reactive antibodies, which have a single broad specificity that corresponds to two or more structurally related antigens or epitopes. For such antibodies the two antigens are related in sequence and structure. For example, antibodies may cross-react with related targets from different species, such as hen egg white lysozyme and turkey lysozyme (WO 92/01047) or with the same target in different states or formats, such as hapten and hapten conjugated to carrier (Griffiths A D et al. EMBO J 1994 13: 14 3245-60). It is possible to deliberately engineer antibodies for cross-reactivity. For example, antibodies have been engineered to recognize two related antigens from different species (example Genentech: antibody binding human LFA1 engineered to also bind rhesus LFA1, resulting in successful drug Raptiva/Efalizumab). Similarly, WO 02/02773 describes antibody molecules with "dual specificity". The antibody molecules referred to are antibodies raised or selected against multiple structurally related antigens, with a single binding specificity that can accommodate two or more structurally related targets. However, as mentioned above, all these cross-reactive antibodies are not truly bi-specific and are not engineered to specifically recognize two unrelated targets.

Furthermore, there are polyreactive autoantibodies, which occur naturally (Casali & Notkins, Ann. Rev. Immunol. 7, 515-531). These polyreactive antibodies have the ability to recognize at least two (usually more) different antigens or epitopes that are not structurally related. It has also been shown that selections of random peptide repertoires using phage display technology on a monoclonal antibody will identify a range of peptide sequences that fit the antigen-binding site. Some of the sequences are highly related, fitting a consensus sequence, whereas others are very different and have been termed mimotopes (Lane & Stephen, Current Opinion in Immunology, 1993, 5, 268-271). It is therefore clear that the binding sites of some heterodimeric VH-VL antibodies have the potential to bind to different and sometimes unrelated antigens. However, as mentioned above, such polyreactive antibodies may be found but have not been deliberately engineered using predictable methods described in the art.

One method described in the art that allows the deliberate engineering of bi-specific antibodies able to bind two structurally unrelated targets through two paratopes, both residing within one complementary heterodimeric VH-VL pair and both comprising CDR residues belonging to this complementary VH-VL pair, relates to "two-in-one" antibodies. These "two-in-one" antibodies are engineered to comprise two overlapping paratopes using methods somewhat distinct from previous cross-reactivity-engineering methods. This work has been described in WO 2008/027236 and by Bostrom et al. (Bostrom et al., Science. 2009 Mar. 20; 323(5921):1610-4). In the published examples, a heterodimeric VH-VL antibody variable region specific for one target (HER2) was isolated and thereafter the light chain was re-diversified to achieve additional specificity for a second target (VEGF or death receptor 5). For one of the resulting antibodies the binding was characterized by structure resolution and it was found that 11 out of 13 VH and VL CDR residues making contact with HER2 in one antibody-antigen complex also made contact with VEGF in the alternative antibody-antigen complex. While the published "two-in-one" antibodies retained nanomolar affinities for HER2, only one of the clones published by Bostrom et al. (2009) had a nanomolar affinity of 300 nM for the additional target, VEGF, while four other clones had micromolar affinities for the additional targets. It is clear that while this approach has achieved binding to two structurally unrelated targets, a degree of surface compatibility between the two targets is needed to enable the specificities of two overlapping paratopes. It also has not been described in detail how highly specific such "two-in-one" antibodies are for only two targets, and whether some general non-specific binding or "stickiness" of such antibodies, potentially caused by the need for some conformational flexibility of side chains located in the overlapping portion of the two paratopes, can be observed.

A second method described in the art that allows the deliberate engineering of bi-specific antibodies able to bind two structurally unrelated targets through two paratopes, both residing within one complementary heterodimeric VH-VL pair and both comprising CDR residues belonging to this complementary VH-VL pair, relates to antibodies comprising complementary pairs of single domain antibodies. WO 2003/002609 and U.S. 2007/026482 have described heterodimeric VH-VL antibodies, in which a heavy chain variable domain recognizes one target and a light chain variable domain recognizes a second structurally unrelated target, and in which the two single domains with different specificities are combined into one joint heterodimeric VH-VL variable region. In the published examples of such antibodies, the single domains were first separately selected as an unpaired VH domain or as an unpaired VL domain to bind the two unrelated targets, and afterwards combined into a joint heterodimeric VH-VL variable region specific to both targets.

For all molecules belonging to the first category of bispecific antibodies (able to bind two targets through two paratopes, both residing within one complementary heterodimeric VH-VL pair and both comprising CDR residues belonging to this complementary VH-VL pair), no additional domains or entities need to be fused to an IgG molecule, no structural loops of an IgG molecule need to be diversified and no limiting hetero-bi-specific Fc regions need to be utilized in order to achieve the dual specificity. This has several potential benefits:

The risk of reducing protein stability is reduced because no structural loops have to be diversified and no constant domain interfaces have to be modified, resulting in potentially greatly improved biophysical properties of the antibodies.

No potentially easily proteolysed or potentially immunogenic linkers are required, resulting in an improved developability of the antibodies as active drug ingredients.

No undesirable pairings of VH and VL domains can occur, avoiding potential byproducts comprising mispaired heterodimeric VH-VL variable regions during expression, because only one unique VH region and one unique VL region is required.

No reduced expression or formation of unusual covalent aggregates are expected, because no additional disulphide bonds are required compared to conventional monospecific antibodies.

The bi-specific heterodimeric variable regions comprising two paratopes within one complementary heterodimeric VH-VL pair can be combined with different constant domains, including Fc regions. This offers several advantages:
  a. Potentially improved manufacturing using fully established methods, for example methods identical to those used in the manufacturing of conventional mono-specific IgGs.
  b. FcRn-mediated serum-half-life modulation in patients and animal models.
  c. Free choice of effector functions associated with different isotypes, ranging from non-cytotoxic, essentially inert behavior (for example in antibodies designed for receptor blockade) to aggressive cytotoxic behavior (for example in antibodies designed to kill tumor cells).

The above third example of "two-in-one" antibodies derived by methods related to cross-reactivity engineering is potentially greatly limited in its medical applicability by competition of the two unrelated targets for the overlapping, at least partially shared binding residues within the CDR loops. Furthermore, the inherently sequential selection process of "two-in-one" antibodies, with specificity first achieved for one target, followed by re-diversification and then discovery of clones specific for an additional target, is time-consuming and unpredictable, because only a limited number of antibodies specific for the first target can be re-diversified into selectable libraries but it is unknown which of the first specific clones will be most amenable to engineering the additional desired specificity. Finally, the isolation and affinity maturation of "two-in-one" antibodies is severely complicated by the fact that any improvement of variable domain sequences to increase binding to one target can potentially cause a reduction in affinity for the other target.

The above fourth example of binding one target through light chain CDR loop residues and another target through heavy chain CDR loop residues is severely complicated by the fact that some of the potentially important light chain CDR residues responsible for binding to the first target are directly adjacent to some of the potentially important heavy chain CDR residues responsible for binding to the second target in the final, packed, bi-specific heterodimeric antibody variable region. This means that in its bound state, the first target recognized by such antibodies can potentially compete with the second target recognized by such antibodies due to steric hindrance, thereby potentially limiting the medical applicability of such antibodies. Furthermore, if light chains and heavy chains of such antibodies are isolated independently by selection and screening methods as was described in the historic example of U.S.2007026482 (Abbott Laboratories), combining them into bi-specific antibodies may potentially affect the affinities of the originally independent domains towards the individual targets in the combined bi-specific molecules due to conformational changes in the CDRs that could potentially occur upon pairing of heavy and light chains. Finally, combining pre-isolated VH and VL variable domains with a variety of CDR loops is likely to result in unpredictable antibody stability, as it has been described by Wörn and Plückthun (1998) and Röthlisberger et al. (2005) that important interactions and a mutual stabilization of antibody heavy and light chains occur between VH and VL domains.

Conversely, the bispecific, heterodimeric variable regions comprising two paratopes within one complementary heterodimeric VH-VL pair could be used as antibody fragments such as Fab fragments or single chain Fvs and would not require the presence of an Fc region to achieve their dual specificity, allowing the option of microbial manufacturing in the absence of mammalian N-glycosylation mechanisms, and their use in therapeutic or diagnostic applications where a low molecular weight or short serum half-life are desirable.

Thus, while the approach of having two paratopes within one complementary heterodimeric VH-VL pair offers so many advantages, the attempts pursued so far, which have been described above, have had limited success.

Thus, there is still a large unmet need to provide an improved format for the bispecific antibodies that incorporates the advantages of having two paratopes within one complementary heterodimeric VH-VL pair, while avoiding the problems observed with the prior art constructs.

The solution for this problem that has been provided by the present invention, i.e. the design of two paratopes for each complementary heterodimeric VH-VL pair, wherein each paratope uses residues from CDR regions from both VH and VL domains, has so far not been achieved or suggested by the prior art.

SUMMARY OF THE INVENTION

The present invention relates to novel bispecific antibodies characterized by having two paratopes for each complementary heterodimeric VH-VL pair, wherein each paratope uses residues from CDR regions from both VH and VL domains.

Thus, in a first aspect, the present invention relates to a method for generating a bispecific antibody or functional bispecific fragment thereof comprising the steps of:
  (A) identifying an antibody or functional fragment thereof with binding specificity for a first target of interest, comprising the steps of contacting (i) the collection of antibodies or functional fragments thereof according to the third aspect of the present invention, or (ii) a collection of antibodies or functional fragments thereof, wherein said collection comprises a diverse collection of antibody variable domain sequences wherein said antibody variable domain sequences comprise a combination of a VL domain and a VH domain,
    a. wherein said VL domain is based on a framework selected from SEQ-ID NOs: 1, 3, 5, and 7, wherein said VL domain is diversified in accordance with the diversification scheme shown in any one of SEQ-ID NOs: 8, 12, 18, 19, 27 or 28; particularly in any one of SEQ-ID NOs: 8, 12, 18, or 19, or in any one of SEQ-ID NOs 27 or 28, and
    b. wherein said VH domain is based on a framework selected from
  SEQ-ID NOs: 2, 4 and 6, wherein said VH domain is diversified in accordance with the diversification scheme shown in any one of SEQ-ID NOs: 9, 13, 20 or 21;

particularly a collection of antibodies or functional fragments thereof selected from any one of the following collections: Lib3-L, Lib4-L, Lib4-LE, and Lib5-L, with said first target of interest and screening or selecting for antibodies or functional fragments thereof with binding specificity for said first target of interest; and (B) identifying an antibody or functional fragment thereof with binding specificity for a first target of interest, comprising the steps of contacting (i) the collection of antibodies or functional fragments thereof according to the second aspect of the present invention, or (ii) a collection of antibodies or functional fragments thereof, wherein said collection comprises a diverse collection of antibody variable domain sequences wherein said antibody variable domain sequences comprise a combination of a VL domain and a VH domain, a. wherein said VL domain is based on a framework selected from SEQ-ID NOs: 1, 3, 5, and 7, wherein said VL domain is diversified in accordance with the diversification scheme shown in any one of SEQ-ID NOs: 10, 14, 16, 22, 23 or 29; particularly in any one of SEQ-ID NOs: 10, 14, 16, 22, or 23, or in SEQ-ID NO 29, and b. wherein said VH domain is based on a framework selected from SEQ-ID NOs: 2, 4 and 6, wherein said VH domain is diversified in accordance with the diversification scheme shown in any one of SEQ-ID NOs: 11, 15, 17, 24, 25 or 26;

particularly a collection of antibodies or functional fragments thereof selected from any one of the following collections: Lib3-H, Lib4-H, Lib4-HE_ini, and Lib4-HE, with said second target of interest and screening or selecting for antibodies or functional fragments thereof with binding specificity for said second target of interest; and (C) combining the paratope specific for an epitope on said first target of one of the antibodies identified in step (A) is combined with the paratope specific for an epitope on said second target of one of the antibodies identified in step (B), provided, however, that the combination of a paratope from an antibody or functional fragment thereof from a collection according to feature c. of the fourth aspect of the present invention with a paratope from an antibody or functional fragment thereof from a collection according to feature c. of the fifth aspect of the present invention is excluded.

In a second aspect the present invention relates to a collection of antibodies or functional fragments thereof, wherein said collection comprises a diverse collection of antibody variable domain sequences comprising at least a Vkappa VL domain and a VH domain, wherein (ia) at least one of the positions Vkappa54 and Vkappa60 is diversified and/or (ib) at least one of the positions VH1 and VH27 is deleted, and (ii) at least 3 additional CDR residues selected from Lib2 positions in accordance with FIG. 1A are diversified, provided that at least one diversified residue is located within the VH domain and at least one diversified position is located within the VL domain, and wherein no residues from Lib1_A positions in accordance with FIG. 1A, particularly no residues from Lib1 positions, are diversified.

In a third aspect, the present invention relates to a collection of antibodies or functional fragments thereof, wherein said collection comprises a diverse collection of antibody variable domain sequences comprising at least a Vkappa VL domain and a VH domain, wherein (ia) at least one of the positions Vkappa4, Vkappa92 and Vkappa97 is diversified and/or (ib) position Vkappa1 is deleted, and (ii) at least 3 additional CDR residues selected from Lib1_A positions in accordance with FIG. 1A are diversified, provided that at least one diversified residue is located within the VH domain and at least one diversified position is located within the VL domain, and wherein no residues from Lib2 in accordance with FIG. 1A are diversified.

In a fourth aspect, the present invention relates to a collection of antibodies or functional fragments thereof, wherein said collection comprises a diverse collection of antibody variable domain sequences wherein said antibody variable domain sequences comprise a combination of a VL domain and a VH domain, a. wherein said VL domain is based on a framework selected from SEQ-ID NOs: 1, 3, 5, and 7, wherein said VL domain is diversified in accordance with the diversification scheme shown in any one of SEQ-ID NOs: 8, 12, 18, 19, 27 or 28; particularly in any one of SEQ-ID NOs: 8, 12, 18, or 19, or in any one of SEQ-ID NOs 27 or 28; and b. wherein said VH domain is based on a framework selected from SEQ-ID NOs: 2, 4 and 6, wherein said VH domain is diversified in accordance with the diversification scheme shown in any one of SEQ-ID NOs: 9, 13, 20 or 21;

a. provided that a combination of a VL domain based on SEQ-ID NO: 1, which is diversified in accordance with the diversification scheme shown in SEQ-ID NOs: 18 or 19, and a VH domain based on SEQ-ID NO: 2, which is diversified in accordance with the diversification scheme shown in SEQ-ID NOs: 20 or 21 is excluded.

In a fifth aspect, the present invention relates to a collection of antibodies or functional fragments thereof, wherein said collection comprises a diverse collection of antibody variable domain sequences wherein said antibody variable domain sequences comprise a combination of a VL domain and a VH domain, a. wherein said VL domain is based on a framework selected from SEQ-ID NOs: 1, 3, 5, and 7, wherein said VL domain is diversified in accordance with the diversification scheme shown in any one of SEQ-ID NOs: 10, 14, 16, 22, 23 or 29; particularly in any one of SEQ-ID NOs: 10, 14, 16, 22, or 23, or in SEQ-ID NO 29; and b. wherein said VH domain is based on a framework selected from SEQ-ID NOs: 2, 4 and 6, wherein said VH domain is diversified in accordance with the diversification scheme shown in any one of SEQ-ID NOs: 11, 15, 17, 24, 25 or 26;

provided that a combination of a VL domain based on SEQ-ID NO: 1, which is diversified in accordance with the diversification scheme shown in SEQ-ID NOs: 22 or 23, and a VH domain based on SEQ-ID NO: 2, which is diversified in accordance with the diversification scheme shown in SEQ-ID NOs: 24, 25 or 26 is excluded.

In a sixth aspect, the present invention relates to a collection of nucleic acid sequences encoding the library according to the present invention.

In a seventh aspect, the present invention relates to a collection of vectors, particularly expression vectors, comprising the collection of nucleic acid sequences of the present invention.

In an eighth aspect, the present invention relates to a collection of host cells comprising the collection of nucleic acid sequences of of the present invention or the collection of vectors according to the present invention.

In a ninth aspect, the present invention relates to a method for producing the collection of antibodies or functional fragments thereof according to any one of the present invention, comprising the step of (i) expressing the nucleic acid sequences of the present invention, (ii) expressing the nucleic acid sequences from the vectors of the present invention, and/or (iii) cultivating the collection of host cells according to of the present invention under conditions that cause or allow the expression of the nucleic acid sequences.

In a tenth aspect, the present invention relates to a method for identifying an antibody or functional fragment thereof with binding specificity for a target of interest, comprising the steps of contacting the collection of antibodies or functional fragments thereof according to any one of the present invention with the target of interest and screening or selecting for antibodies or functional fragments thereof with binding specificity for said target of interest.

In an eleventh aspect, the present invention relates to an antibody or functional fragment that is obtainable by the method of the present invention.

In a twelfth eleventh aspect, the present invention relates to a bispecific antibody or functional bispecific fragment thereof that is obtainable by the method of the present invention.

In a final aspect, the present invention relates to pharmaceutical compositions comprising an antibody molecule or functional fragment thereof, or a bispecific antibody or bispecific functional fragment thereof, of the present invention and optionally a pharmaceutically acceptable carrier and/or excipient.

BRIEF DESCRIPTION OF THE DRAWINGS

FIG. 2 also illustrates in a schematic way the location of those potential enhancing residues according to the current invention in the framework regions that are visible from the top view (aerial) perspective.

FIG. 3 further shows three additional preferred library designs (Lib D1H3, Lib D2L1and Lib D2H1). The following SEQ ID NOs: correspond to the following sequences shown in FIG. 3: Dummy 1 VK (SEQ ID NO: 1), Dummy 1VH (SEQ ID NO: 2), Dummy 2VL (SEQ ID NO: 30), Lib D2L1 VL (SEQ ID NO: 31), Dummy 2 VH (SEQ ID NO: 32), Lib D2L1 VH (SEQ ID NO: 33), Lib D2H1 VL (SEQ ID NO: 34), and Lib D2H1 VH (SEQ ID NO: 35).

FIG. 9 shows an overview of the library frameworks (or scaffolds) being used in accordance with the present invention.

FIG. 10 shows an overview of the diversification strategies used in accordance with the present invention. Residues "X" are residues that are diversified. Residues showing an " X " in strikethrough and bold are deleted in some clones of the library, thus creating length variability.

DETAILED DESCRIPTION OF THE INVENTION

Figure 1:
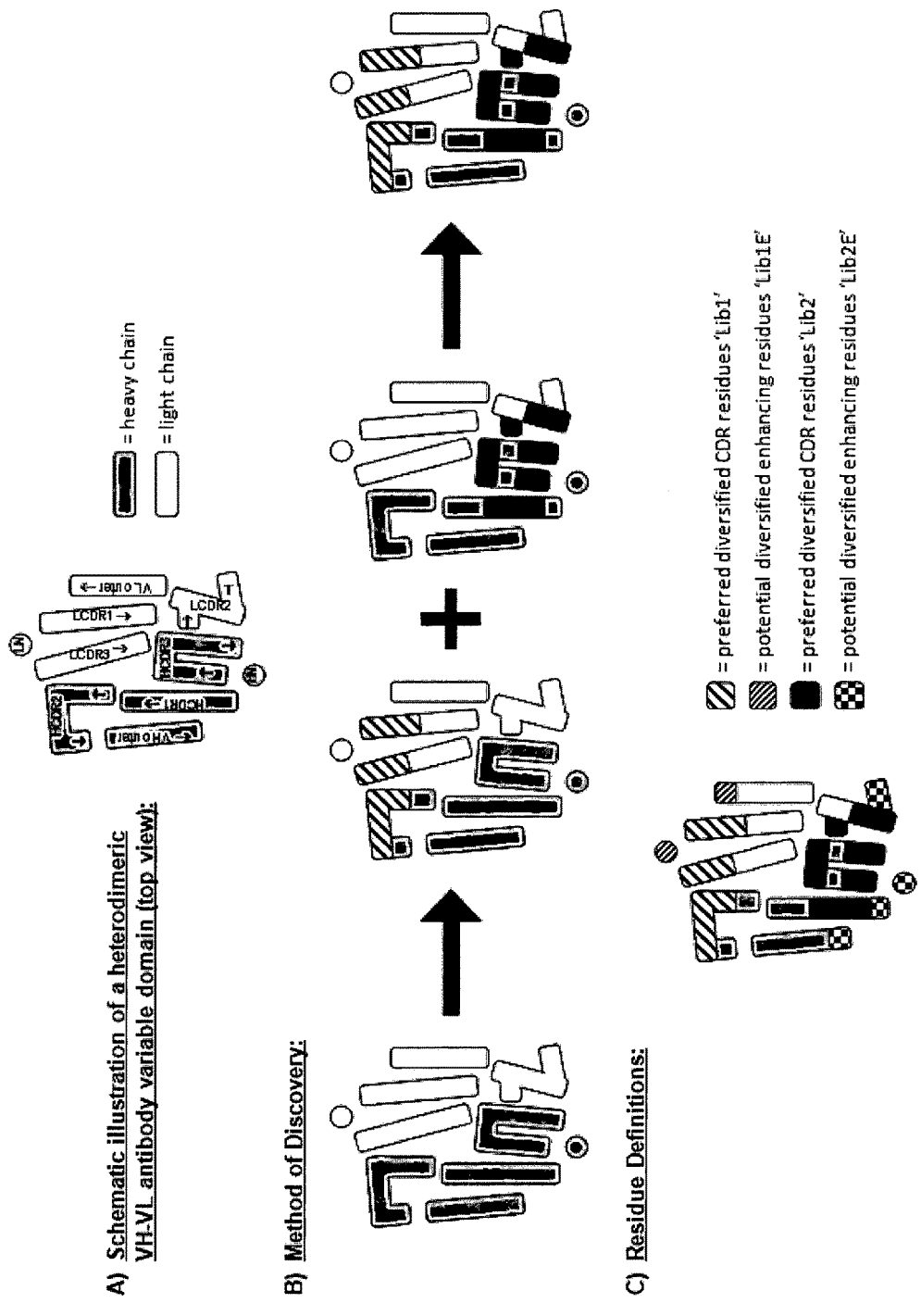
FIG. 1 below shows the list of preferred CDR positions of which all or a subset should be diversified in antibody libraries in some embodiments of our present invention (A), the list of preferred optional enhancing positions in the framework regions which may also be diversified in antibody libraries in some embodiments of the invention (B), and the list of CDR positions of which all or a subset are preferably left invariant in all libraries of the present invention, i.e. both in libraries in which Lib1 or Lib1_A residues are diversified and in libraries in which Lib2 residues are diversified (C).
Figure 2:
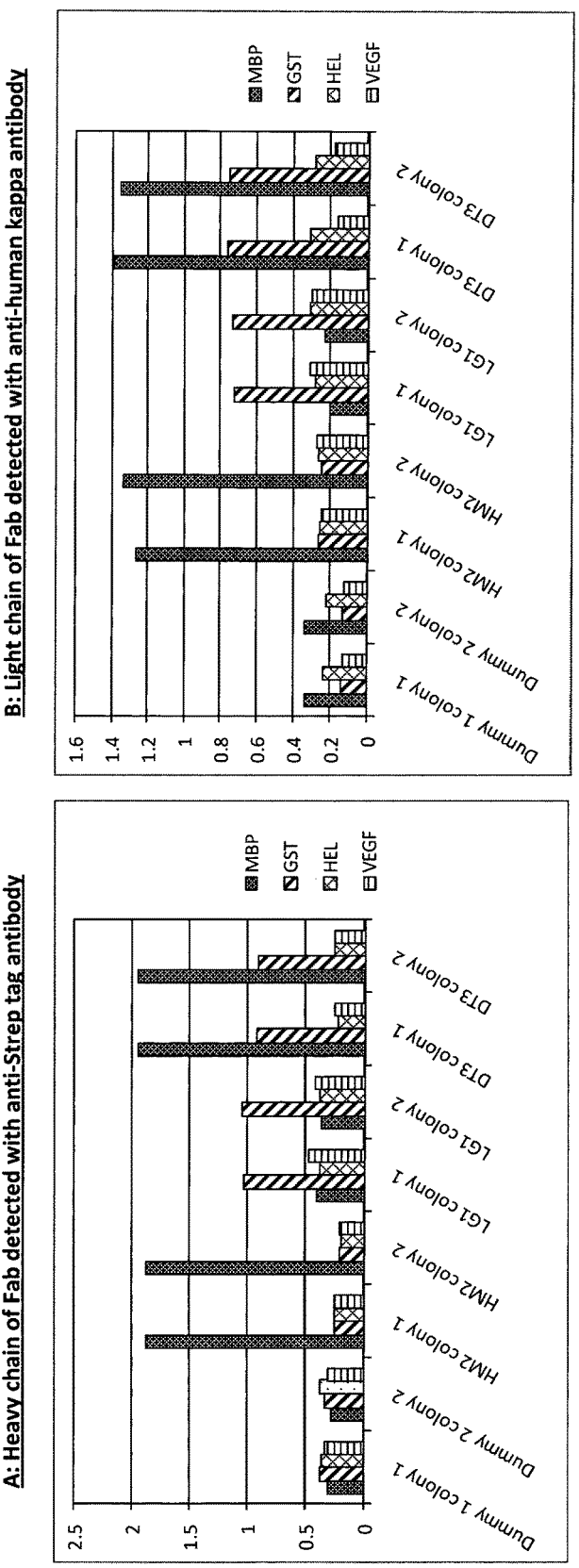
FIG. 2 below illustrates in a schematic way the discovery process of the novel bi-specific antibodies, using the top view (aerial) perspective to show how a heterodimeric VH-VL antibody scaffold is first diversified separately in two regions representing Lib1 or Lib1 _A and Lib2 CDR residues; this yields two libraries that are separately selected to obtain two antibody clones, with one clone binding a first target or epitope via a first paratope and the second clone binding a second target or epitope via a second paratope; these clones are then combined into a bi-specific antibody according to the present invention, by introducing target-specific residues selected in Lib1 or Lib1 _A positions in the first antibody clone into the second antibody clone, or by introducing target-specific residues selected in Lib2 positions in the second antibody clone into the first antibody clone.
Figure 3:
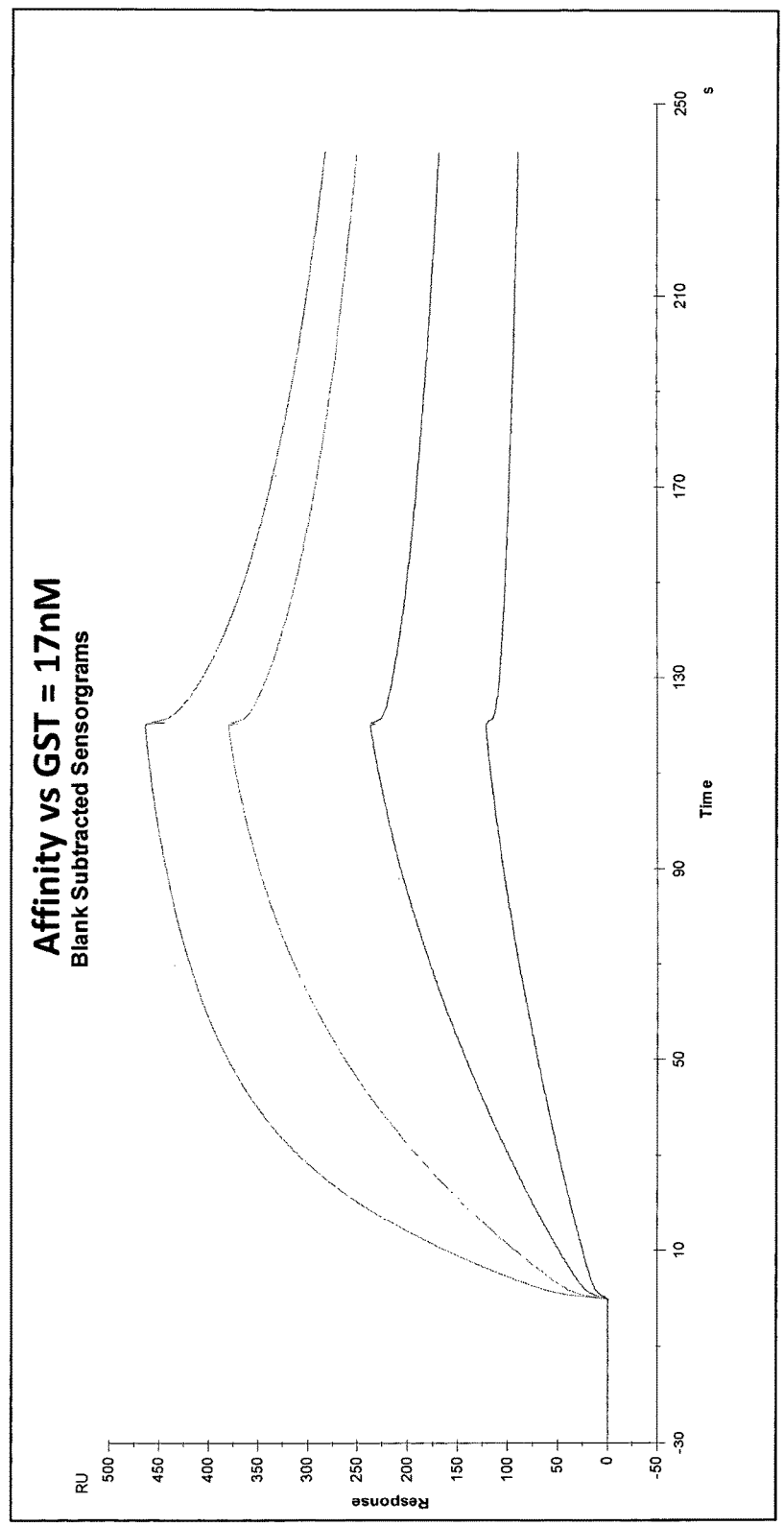
FIG. 3 shows four initial library designs (libraries Lib D1L1, Lib D1L2, Lib D1H1 and Lib D1H2), which we have tested. We have produced each of these four libraries as a pool of synthetic genes encoding human Fab fragments with the shown VH3-VK1 pairing as heterodimeric VH-VL scaffold. The synthetic genes in each library were constant in the positions for which a specific amino acid is displayed in the single letter code, and diversified in the positions marked by "X". The four libraries were each produced as phage display libraries and sorted against several antigens using standard methods known in the art. Selected antibody clones from these four libraries have been combined into the bi-specific antibodies detailed in FIG. 4.

The peculiarity of this invention compared to former approaches for the construction of bispecific antibodies is the so far unknown possibility to have two paratopes for each complementary heterodimeric VH-VL pair, wherein each paratope uses residues from CDR regions from both VH and VL domains.

Thus, the present application relates to an antibody or functional fragment thereof comprising at least one variable binding domain consisting of a heavy chain variable (VH) domain and a light chain variable (VL) domain, wherein said binding domain comprises two paratopes for two unrelated epitopes, wherein (i) binding of each paratope to its epitope does not prevent the simultaneous binding of the other paratope to its respective epitope, and wherein (ii) both paratopes comprise at least one residue from at least one VH CDR and at least one residue from at least one VL CDR.

Thus, in a first aspect, the present invention relates to a method for generating a bispecific antibody or functional bispecific fragment thereof comprising the steps of:

(A) identifying an antibody or functional fragment thereof with binding specificity for a first target of interest, comprising the steps of contacting (i) the collection of antibodies or functional fragments thereof according to the third aspect of the present invention, or (ii) a collection of antibodies or functional fragments thereof, wherein said collection comprises a diverse collection of antibody variable domain sequences wherein said antibody variable domain sequences comprise a combination of a VL domain and a VH domain,
  c. wherein said VL domain is based on a framework selected from SEQ-ID NOs: 1, 3, 5, and 7, wherein said VL domain is diversified in accordance with the diversification scheme shown in any one of SEQ-ID NOs: 8, 12, 18, 19, 27 or 28; particularly in any one of SEQ-ID NOs: 8, 12, 18, or 19, or in any one of SEQ-ID NOs 27 or 28, and
  d. wherein said VH domain is based on a framework selected from SEQ-ID NOs: 2, 4 and 6, wherein said VH domain is diversified in accordance with the diversification scheme shown in any one of SEQ-ID NOs: 9, 13, 20 or 21;
  particularly a collection of antibodies or functional fragments thereof selected from any one of the following collections: Lib3-L, Lib4-L, Lib4-LE, and Lib5-L, with said first target of interest and screening or selecting for antibodies or functional fragments thereof with binding specificity for said first target of interest; and (B) identifying an antibody or functional fragment thereof with binding specificity for a first target of interest, comprising the steps of contacting (i) the collection of antibodies or functional fragments thereof according to the second aspect of the present invention, or (ii) a collection of antibodies or functional fragments thereof, wherein said collection comprises a diverse collection of antibody variable domain sequences wherein said antibody variable domain sequences comprise a combination of a VL domain and a VH domain,
  c. wherein said VL domain is based on a framework selected from SEQ-ID NOs: 1, 3, 5, and 7, wherein said VL domain is diversified in accordance with the diversification scheme shown in any one of SEQ-ID NOs: 10, 14, 16, 22, 23 or 29; particularly in any one of SEQ-ID NOs: 10, 14, 16, 22, or 23, or in SEQ-ID NO 29, and
  d. wherein said VH domain is based on a framework selected from SEQ-ID NOs: 2, 4 and 6, wherein said VH domain is diversified in accordance with the diversification scheme shown in any one of SEQ-ID NOs: 11, 15, 17, 24, 25 or 26;
  particularly a collection of antibodies or functional fragments thereof selected from any one of the following collections: Lib3-H, Lib4-H, Lib4-HE_ini, and Lib4-HE, with said second target of interest and screening or selecting for antibodies or functional fragments thereof with binding specificity for said second target of interest; and (C) combining the paratope specific for an epitope on said first target of one of the antibodies identified in step (A) is combined with the paratope specific for an epitope on said second target of one of the antibodies identified in step (B),
  provided, however, that the combination of a paratope from an antibody or functional fragment thereof from a collection according to feature c. of the fourth aspect of the present invention with a paratope from an antibody or functional fragment thereof from a collection according to feature c. of the fifth aspect of the present invention is excluded.

In certain embodiments of the first aspect, the present invention relates to a method, further comprising the step of:

(D) expressing nucleic acid sequence encoding the bispecific antibody or functional bispecific fragment thereof generated in steps (A) to (C) in a host cell or translating the nucleic acid into protein representing the bispecific antibody or functional bispecific fragment thereof.

In a second aspect the present invention relates to a collection of antibodies or functional fragments thereof, wherein said collection comprises a diverse collection of antibody variable domain sequences comprising at least a Vkappa VL domain and a VH domain, wherein (ia) at least one of the positions Vkappa54 and Vkappa60 is diversified and/or (ib) at least one of the positions VH1 and VH27 is deleted, and (ii) at least 3 additional CDR residues selected from Lib2 positions in accordance with FIG. 1A are diversified, provided that at least one diversified residue is located within the VH domain and at least one diversified position is located within the VL domain, and wherein no residues from Lib1_A positions in accordance with FIG. 1A, particularly no residues from Lib1 positions, are diversified.

In particular embodiments of the second aspect, the invention relates to a collection, wherein in (i), position Vkappa60 is diversified, but not position Vkappa54.

In particular embodiments of the second aspect, the invention relates to a collection, wherein in (i), position Vkappa60 is diversified, but not position Vkappa54.

In particular embodiments of the second aspect, the invention relates to a collection, wherein in (i), position Vkappa54 is diversified, but not position Vkappa60.

In particular embodiments of the second aspect, the invention relates to a collection, wherein in (i), both positions Vkappa54 and Vkappa54 are diversified.

In particular embodiments of the second aspect, the invention relates to a collection, wherein at least one residue of each of CDR1 and CDR3 of the VH domain and CDR2 of the VL domain is diversified.

In particular embodiments of the second aspect, the invention relates to a collection, wherein at least one residue of the Lib2E_A positions in accordance with FIG. 1B; particularly at least one residue from Lib2E positions, is additionally diversified in said variable binding domain.

In particular embodiments of the second aspect, the invention relates to a collection, wherein at least 14 residues are diversified in VL and VH, particularly wherein at least 4 residues are diversified in VL CDR2, and at least 10 residues are diversified in VH CDR1 and VH CDR3.

In particular embodiments of the second aspect, the invention relates to a collection, wherein 15, 16, 17, 18, 19 or 20 residues are diversified.

In a third aspect, the present invention relates to a collection of antibodies or functional fragments thereof, wherein said collection comprises a diverse collection of antibody variable domain sequences comprising at least a Vkappa VL domain and a VH domain, wherein (ia) at least one of the positions Vkappa4, Vkappa92 and Vkappa97 is diversified and/or (ib) position Vkappa1 is deleted, and (ii) at least 3 additional CDR residues selected from Lib1_A positions in accordance with FIG. 1A are diversified, provided that at least one diversified residue is located within the VH domain and at least one diversified position is located within the VL domain, and wherein no residues from Lib2 in accordance with FIG. 1A are diversified.

In particular embodiments of the third aspect, the invention relates to a collection, wherein in (i), position Vkappa4 is diversified, but not position Vkappa92 or position Vkappa97.

In particular embodiments of the third aspect, the invention relates to a collection, wherein in (i), position Vkappa92 is diversified, but not position Vkappa4 or position Vkappa97.

In particular embodiments of the third aspect, the invention relates to a collection, wherein in (i), position Vkappa97 is diversified, but not position Vkappa4 or position Vkappa92.

In particular embodiments of the third aspect, the invention relates to a collection, wherein in (i), two positions selected from Vkappa4, Vkappa92 and Vkappa92 are diversified.

In particular embodiments of the third aspect, the invention relates to a collection, wherein in (i), all three positions Vkappa4, Vkappa92 and Vkappa92 are diversified.

In particular embodiments of the third aspect, the invention relates to a collection, wherein at least one residue of each of CDR1 and CDR3 of the VL domain and CDR2 of the VH domain is diversified.

In particular embodiments of the third aspect, the invention relates to a collection, wherein at least one residue of the Lib1E_A positions in accordance with FIG. 1B is additionally diversified in said variable binding domain.

In particular embodiments of the third aspect, the invention relates to a collection, wherein at least 14 residues are diversified in VL and VH, particularly wherein at least 4 residues are diversified in VH CDR2, and at least 10 residues are diversified in VL CDR1 and VL CDR3.

In particular embodiments of the third aspect, the invention relates to a collection, wherein 15, 16, 17, 18, 19 or 20 residues are diversified.

In a fourth aspect, the present invention relates to a collection of antibodies or functional fragments thereof, wherein said collection comprises a diverse collection of antibody variable domain sequences wherein said antibody variable domain sequences comprise a combination of a VL domain and a VH domain,
a. wherein said VL domain is based on a framework selected from SEQ-ID NOs: 1, 3, 5, and 7, wherein said VL domain is diversified in accordance with the diversification scheme shown in any one of SEQ-ID NOs: 8, 12, 18, 19, 27 or 28; particularly in any one of SEQ-ID NOs: 8, 12, 18, or 19, or in any one of SEQ-ID NOs 27 or 28; and
b. wherein said VH domain is based on a framework selected from SEQ-ID NOs: 2, 4 and 6, wherein said VH domain is diversified in accordance with the diversification scheme shown in any one of SEQ-ID NOs: 9, 13, 20 or 21;
provided that a combination of a VL domain based on SEQ-ID NO: 1, which is diversified in accordance with the diversification scheme shown in SEQ-ID NOs: 18 or 19, and a VH domain based on SEQ-ID NO: 2, which is diversified in accordance with the diversification scheme shown in SEQ-ID NOs: 20 or 21 is excluded In particular embodiments of the fourth aspect, the invention relates to a collection, which is selected from any one of the following collections: Lib3-L, Lib4-L, Lib4-LE, and Lib5-L In a fifth aspect, the present invention relates to a collection of antibodies or functional fragments thereof, wherein said collection comprises a diverse collection of antibody variable domain sequences wherein said antibody variable domain sequences comprise a combination of a VL domain and a VH domain,
c. wherein said VL domain is based on a framework selected from SEQ-ID NOs: 1, 3, 5, and 7, wherein said VL domain is diversified in accordance with the diversification scheme shown in any one of SEQ-ID NOs: 10, 14, 16, 22, 23 or 29; particularly in any one of SEQ-ID NOs: 10, 14, 16, 22, or 23, or in SEQ-ID NO 29; and
d. wherein said VH domain is based on a framework selected from SEQ-ID NOs: 2, 4 and 6, wherein said VH domain is diversified in accordance with the diversification scheme shown in any one of SEQ-ID NOs: 11, 15, 17, 24, 25 or 26;
provided that a combination of a VL domain based on SEQ-ID NO: 1, which is diversified in accordance with the diversification scheme shown in SEQ-ID NOs: 22 or 23, and a VH domain based on SEQ-ID NO: 2, which is diversified in accordance with the diversification scheme shown in SEQ-ID NOs: 24, 25 or 26 is excluded.

In particular embodiments of the fifth aspect, the invention relates to a collection, which is selected from any one of the following collections: Lib3-H, Lib4-H, Lib4-HE_ini, and Lib4-HE.

In a sixth aspect, the present invention relates to a collection of nucleic acid sequences encoding the library according to the present invention.

In a seventh aspect, the present invention relates to a collection of vectors, particularly expression vectors, comprising the collection of nucleic acid sequences of the present invention.

In particular embodiments, said vectors are phage display vectors

In an eighth aspect, the present invention relates to a collection of host cells comprising the collection of nucleic acid sequences of of the present invention or the collection of vectors according to the present invention.

In a ninth aspect, the present invention relates to a method for producing the collection of antibodies or functional fragments thereof according to any one of the present invention, comprising the step of (i) expressing the nucleic acid sequences of the present invention, (ii) expressing the nucleic acid sequences from the vectors of the present invention, and/or (iii) cultivating the collection of host cells according to of the present invention under conditions that cause or allow the expression of the nucleic acid sequences.

In a tenth aspect, the present invention relates to a method for identifying an antibody or functional fragment thereof with binding specificity for a target of interest, comprising the steps of contacting the collection of antibodies or functional fragments thereof according to any one of the present invention with the target of interest and screening or selecting for antibodies or functional fragments thereof with binding specificity for said target of interest.

In particular embodiments, said screening or selecting is using phage display.

In certain embodiments of the tenth aspect, the present invention relates to a method, further comprising the step of:

expressing nucleic acid sequence encoding the antibody or functional fragment thereof with binding specificity for a target of interest in a host cell or translating the nucleic acid into protein representing the antibody or functional fragment thereof with binding specificity for a target of interest.

In an eleventh aspect, the present invention relates to an antibody or functional fragment that is obtainable by the method of the present invention.

In a twelfth aspect, the present invention relates to a bispecific antibody or functional bispecific fragment thereof that is obtainable by the method of the present invention.

In a final aspect, the present invention relates to pharmaceutical compositions comprising an antibody molecule or functional fragment thereof, or a bispecific antibody or bispecific functional fragment thereof, of the present invention and optionally a pharmaceutically acceptable carrier and/or excipient.

As used herein, the term "antibody" refers to an immunoglobulin (Ig) molecule that is defined as a protein belonging to the class IgG, IgM, IgE, IgA, or IgD (or any subclass thereof), which includes all conventionally known antibodies and functional fragments thereof. A "functional fragment" of an antibody/immunoglobulin molecule hereby is defined as a fragment of an antibody/immunoglobulin molecule (e.g., a variable region of an IgG) that retains the antigen-binding region. An "antigen-binding region" of an antibody typically is found in one or more hypervariable region(s) (or complementarity-determining region, "CDR") of an antibody molecule, i.e. the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of antibody molecules for use in the present invention is IgG.

"Functional fragments" of the invention include the domain of a F(ab')2 fragment, a Fab fragment, scFv or constructs comprising single immunoglobulin variable domains or single domain antibody polypeptides, e.g. single heavy chain variable domains or single light chain variable domains. The F(ab')2 or Fab may be engineered to minimize or completely remove the intermolecular disulphide interactions that occur between the CH1 and CL domains.

An antibody may be derived from immunizing an animal, or from a recombinant antibody library, including an antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al.

In the context of the present invention, the term "bispecific antibody molecule" refers to an antibody molecule, including a functional fragment of an antibody molecule, that comprises specific binding sites for two different target biomolecules, or two different epitopes, either present on one target biomolecule, or present on two different molecules, such as on the target biomolecule and a second biomolecule.

As used herein, a binding molecule is "specific to/for", "specifically recognizes", or "specifically binds to" a target, such as a target biomolecule (or an epitope of such biomolecule), when such binding molecule is able to discriminate between such target biomolecule and one or more reference molecule(s), since binding specificity is not an absolute, but a relative property. In its most general form (and when no defined reference is mentioned), "specific binding" refers to the ability of the binding molecule to discriminate between the target biomolecule of interest and an unrelated biomolecule, as determined, for example, in accordance with specificity assay methods known in the art. Such methods comprise, but are not limited to Western blots, ELISA, RIA, ECL, IRMA tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. Typically, determination of binding specificity is performed by using not a single reference biomolecule, but a set of about three to five unrelated biomolecules, such as milk powder, BSA, transferrin or the like.

In the context of the present invention, the term "about" or "approximately" means between 90% and 110% of a given value or range.

However, "specific binding" also may refer to the ability of a binding molecule to discriminate between the target biomolecule and one or more closely related biomolecule(s), which are used as reference points. Additionally, "specific binding" may relate to the ability of a binding molecule to discriminate between different parts of its target antigen, e.g. different domains, regions or epitopes of the target biomolecule, or between one or more key amino acid residues or stretches of amino acid residues of the target biomolecule.

In the context of the present invention, the term "paratope" refers to that part of a given antibody molecule that is required for specific binding between a target and the antibody molecule. A paratope may be continuous, i.e. formed by adjacent amino acid residues present in the antibody molecule, or discontinuous, i.e. formed by amino acid residues that are at different positions in the primary sequence of the amino acid residues, such as in the amino acid sequence of the CDRs of the amino acid residues, but in close proximity in the three-dimensional structure, which the antibody molecule adopts.

In the context of the present invention, the term "epitope" refers to that part of a given target that is required for specific binding between the target and an antibody. An epitope may be continuous, i.e. formed by adjacent structural elements present in the target, or discontinuous, i.e. formed by structural elements that are at different positions in the primary sequence of the target, such as in the amino acid sequence of a protein as target, but in close proximity in the three-dimensional structure, which the target adopts in a native environment, such as in a bodily fluid.

In one embodiment, the antibody or functional fragment thereof is a bispecific antibody.

In further embodiments of the antibody or functional fragment of the present invention, the amount of binding of each paratope to its respective epitope in the simultaneous presence of both epitopes is at least 25% of the amount of binding that is achieved in the absence of the other epitope under otherwise identical conditions.

In further embodiments of the antibody or functional fragment of the present invention, the amount of binding is at least 50%, particularly at least 75%, and more particularly at least 90%.

In further embodiments of the antibody or functional fragment of the present invention, the first paratope comprises residues from CDR1 and CDR3 of the VL domain and CDR2 of the VH domain, and the second paratope comprises residues from CDR1 and CDR3 of the VH domain and CDR2 of the VL domain.

In particular embodiments, the antibody or functional fragment thereof is a human antibody or functional fragment thereof.

In further embodiments, the antibody or functional fragment of the present invention is based on a human VH3 family heavy chain sequence and a human Vkappa1 family light chain sequence.

In further embodiments, the antibody or functional fragment of the present invention is based on a human VH3 family heavy chain sequence and a human Vlambda1 family light chain.

In further embodiments, the antibody or functional fragment of the present invention is selected from a single chain Fv fragment, a Fab fragment and an IgG.

In further embodiments of the antibody or functional fragment thereof of the invention, binding to one epitope can be knocked out by mutating either (i) one of the Lib1 or Lib1_A positions or (ii) one of the Lib2 positions, while binding to the other epitope is kept intact.

In this context, the phrase "binding . . . [is] . . . knocked out" refers to a situation where the affinity to the epitope is reduced at least 10-fold (e.g. from 1 nM to 10 nM), and the phrase "binding . . . is kept intact" refers to a situation where the affinity to the epitope is reduced at maximum 3-fold (e.g. from 1 nM to 3 nM).

In particular such embodiments, binding to one epitope can be knocked out by mutating one of the positions VL position 27 or VH position 61, or by mutating one of the Lib2 positions VL position 56 or VH position 28.

In particular such embodiments, binding to one epitope can be knocked out by mutating one of the residues listed in section [0110] to R, when the residue is selected from D, N, E and Q, or by mutating such residue to D, when the residue is different from D, N, E or Q.

Thus, the present invention relates to a binding molecule comprising at least one antibody variable domain comprising one variable light chain and one variable heavy chain, wherein said antibody variable domain is binding to at least a first and a second target, wherein binding of said antibody variable domain to said first target is independent from binding of said antibody variable domain to said second target and vice versa, and wherein said first and second target are neither anti-idiotypic antibodies, nor non-physiological peptides, such as peptides used for epitope mapping.

In the context of the present invention, binding of the antibody variable domain to one target is "independent" from binding to the other target, when the amount of binding of the first paratope to its respective epitope (the first target) in the simultaneous presence of both targets is at least 25% of the amount of binding that is achieved in the absence of the other target under otherwise identical conditions. In particular, the amount of binding is at least 50%, particularly at least 75%, and more particularly at least 90%.

In particular embodiments, said first and said second target are both physiologically relevant targets and/or epitopes thereof, including disease-related targets, such as cancer-related antigens, cell surface receptors, cytokines and/or other signaling molecules.

In another aspect, the present invention relates to nucleic acid sequence encoding the antibody or functional fragment thereof according to the present invention.

In another aspect, the present invention relates to a vector comprising the nucleic acid sequence according to the present invention.

In another aspect, the present invention relates to a host cell comprising the nucleic acid sequence according to the present invention, or the vector according to the present invention.

In another aspect, the present invention relates to a method for generating the antibody or functional fragment thereof according to the present invention, comprising the step of expressing the nucleic acid sequence according to the present invention, or the vector according to the present invention, either in vitro or from an appropriate host cell, including the host cell according to the present invention.

In certain such embodiments, the antibody molecule or functional fragment thereof is selected from a single chain Fv fragment, a Fab fragment and an IgG.

In a final aspect, the present invention relates to pharmaceutical compositions comprising an antibody molecule or functional fragment thereof, or a bispecific antibody or bispecific functional fragment thereof, of the present invention and optionally a pharmaceutically acceptable carrier and/or excipient. The compositions may be formulated e.g. for once-a-day administration, twice-a-day administration, or three times a day administration.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

In the context of the present invention, the term "about" or "approximately" means between 90% and 110% of a given value or range. In particular embodiments, the term means between 95% and 105% of a given value or range. In particular embodiments, the term means 100% of a given value or range.

The term "carrier" applied to pharmaceutical compositions of the invention refers to a diluent, excipient, or vehicle with which an active compound (e.g., a bispecific antibody fragment) is administered. Such pharmaceutical carriers may be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, 20th Edition.

The active ingredient (e.g., a bispecific antibody fragment) of the composition of the present invention may be used for the treatment of at least one disease or disorder, wherein the treatment is adapted to or appropriately prepared for a specific administration as disclosed herein (e.g., to once-a-day, twice-a-day, or three-times-a-day administration). For this purpose the package leaflet and/or the patient information contains corresponding information.

The active ingredient (e.g., the bispecific antibody molecule or bispecific fragment thereof) of the composition of the present invention may be used for the manufacture of a medicament for the treatment of at least one disease or disorder, wherein the medicament is adapted to or appropriately prepared for a specific administration as disclosed herein (e.g., to once-a-day, twice-a-day, or three-times-a-day administration). For this purpose the package leaflet and/or the patient information contains corresponding information.

EXAMPLES

The following examples illustrate the invention without limiting its scope.

While the first category of bi-specific antibody molecules described above (with two paratopes specific for two targets which both comprise CDR residues located within the same heterodimeric VH-VL antibody variable region) offers a range of potential benefits as described above, we hypothesized that an entirely novel class of antibody molecule could be created, that belongs to this first category of antibody molecules but is entirely different from the above-mentioned four examples that have been reported in the literature. We hypothesized that by pursuing an entirely novel approach, it might be possible to achieve some dramatic improvements in the deliberate engineering of antibodies belonging to this first category, compared to the examples mentioned above. This hypothesis took into account the fact that the historic methods mentioned above have some significant potential limitations in the development of antibodies as active drug ingredients.

According to the present invention, we describe an entirely novel class of bi-specific antibodies, which address these issues and have unexpected and dramatic advantages. We speculated that it may be possible to engineer two distinct paratopes within the VH-VL variable region of a heterodimeric antibody, each comprising CDR residues from both the heavy chain and the light chain, but not overlapping and preferably not immediately adjacent to each other, in order to avoid conformational changes in one binding site as a result of mutations in the other binding site, and in order to reduce the likelihood of competition between the two targets in binding to the antibody (by minimizing possible steric hindrance between the two targets in their bound state). We further speculated that this novel class of antibody molecule could be engineered by first creating two synthetic antibody libraries, each in the background of a packed heterodimeric VH-VL pair, in one of which a first set (Lib1 or Lib1 A) of heavy and light chain CDR positions could be diversified and in the other one of which a different, non-overlapping set (Lib2) of heavy and light chain CDR positions could be diversified. We concluded that if such libraries could be created and successfully selected in parallel against two unrelated targets, then bi-specific antibodies could potentially be created rapidly by introducing the specific residues selected in the Lib1 positions during selections against the first target, into an antibody clone with specific residues selected in the Lib2 positions during selections against the second target. Vice versa, we also concluded that if such libraries could be created and successfully selected against two distinct targets, then bi-specific antibodies could potentially be created by introducing the residues selected in the Lib2 positions during selections against the second target into an antibody clone with specific residues selected in the Lib1 or Lib1 _A positions during selections against the first target. We speculated that this strategy of introducing a set of residues from a first antibody, defining a first specificity, into a second antibody of a second specificity would be greatly helped by creating both libraries within an identical or highly similar scaffold defining the packed VH-VL pair.

In the present application we demonstrate that we have successfully implemented this invention, creating several bi-specific heterodimeric VH-VL antibodies against two completely unrelated targets. Importantly, the antibodies were rapidly created and were highly specific for only two targets, showing no binding to additional unrelated targets. Surprisingly, the created bispecific antibodies showed not only a high biophysical stability (that has not been demonstrated for antibodies binding one target through light chain CDR loop residues and another target through heavy chain CDR loop residues), but an extremely high biophysical stability even compared to the scaffold used in the creation of "two-in-one" antibodies and compared to established monospecific antibody clones used as active ingredients in marketed drugs. Finally and also surprisingly, using the example of a bi-specific antibody against GM-CSF and TNF-alpha, we were able to demonstrate that a single conservative point mutation in a CDR position within the Lib1 or Lib1 _A binding region providing the putative paratope involved in TNF-alpha-binding essentially abolished binding to TNF-alpha whilst leaving binding to GM-CSF intact, and that a different single conservative point mutation in a CDR position within the Lib2 binding region providing the putative paratope involved in GM-CSF-binding completely abolished binding to GM-CSF whilst leaving binding to TNF-alpha intact. This demonstrates that the antibodies of Our current invention can indeed bind two unrelated targets in a highly specific manner, rather than through general "stickiness", and that in contrast to above bi-specific antibodies known in the art, the two binding sites that are designed as non-overlapping paratopes are essentially independently behaved, although both are located in one heterodimeric VH-VL variable region and although both comprise CDR residues belonging to the same heterodimeric variable region. The antibodies of the present invention therefore have key advantages over prior bi-specific antibodies.

In preferred embodiments of the present invention, the preferred discovery process comprises the steps of (1) generating a pair of libraries based on the same or a highly similar heterodimeric VH-VL antibody scaffold by diversification of different CDR positions in the first and second library, (2) optionally also including diversification of selected framework positions in the VH-VL scaffold in one or both of the two libraries to potentially enhance the binding properties of clones selected from the two libraries, (3) selecting both libraries independently against two target molecules or epitopes and characterizing binders to identify target- or epitope-specific antibody clones with desired properties, (4) introducing all of the residues or a subset of the residues (preferably the majority of residues but no less than 3 of the residues) selected in diversified positions in an antibody clone selected from one library and specific for a first target or epitope into a target-specific antibody clone selected from the other library and specific for a second target or epitope. For this discovery process to work optimally, some groups of key residues play an important role:

By examining molecular models of heterodimeric VH-VL antibodies in silico and by performing mutagenesis of unselected heterodimeric VH-VL antibody "dummies" with no specificity (data not shown), we derived a list of CDR residues that could potentially be diversified to form the first potential binding site against the first target (Lib1 or Lib1 _A residues) and a list of CDR residues that could potentially be diversified to form the second potential binding site against the second target (Lib2 residues). We also derived a list of potential enhancing residues in the antibody framework regions, which in the folded antibody molecule are in close proximity to the Lib1, Lib1 _A or Lib2 CDR residues and which can potentially be diversified to modify the properties and enhance the binding of the first paratope comprising Lib1 or Lib1 _A CDR residues to a first target (Lib1E or Lib1E_A enhancing residues) and the binding of the second paratope comprising Lib2 CDR residues to a second target (Lib2E or Lib2E_A enhancing residues). Finally, we derived a list of CDR residues that would preferably be left identical or very similar in both libraries, to maintain an invariant packing of a central core region of the antibody molecule in both libraries, which would then also be present in all combined bi-specific antibody clones comprising a set of target-1-specific Lib1 or Lib1_A and optionally Lib1 E or Lib1E_A residues as well as a set of target-2-specific Lib2 and optionally Lib2E or Lib2E_A residues. We concluded that this invariant packed core region would shield the two binding sites from each other, making the first paratope against the first target somewhat immune to detrimental conformational effects resulting from changes in the second paratope against the second target. Indeed we have been able to demonstrate that the affinities and binding kinetics of parental antibody clones are usually closely matched by combined bi-specific antibody clones derived from the parental clones. Example 8 illustrates this using the exemplary antigens VEGF and IL6 where parental antibodies IL6P with an affinity of 38 nM and VEGFP with an affinity of 11 nM were combined to yield the bi-specific antibody VH6L with an affinity of 40 nM for IL6 and 7.8 nM for VEGF. This surprisingly high level of independence of the two binding sites makes it possible to affinity-mature them and in parallel in a way not possible for "two-in-one" antibodies (third historic example above) or bi-specific paired single domain heterodimers (fourth historic example above). We also concluded that the invariant core region may achieve a spacing between the two binding sites, potentially allowing them to bind two targets independently without competition caused by overlapping paratopes or by steric hindrance between a first bound and a second unbound target, depending on the nature and molecular size of each target molecule. Indeed, using the exemplary antigens GMCSF and IL6, we have been able to demonstrate for the novel class of bi-specific antibody molecules according to the invention that for some of the combined clones, co-binding of both antigens to a single VH-VL variable region is possible. Moreover, Example 9 illustrates that the affinity of the co-binding of the second antigen to the variable region can be independent of whether the first target is present or absent. The possibility of achieving such co-binding to the same VH-VL variable region and the possible independence of co-binding affinities have not been demonstrated for other types of historic bi-specific antibodies and represent a unique advantage of the novel antibodies according to the present invention. In some of the novel bi-specific antibodies, the independent binding behavior can further be demonstrated by mutations like those listed in Example 10. In such antibodies, it is possible to knock out or greatly reduce affinity for a first target whilst leaving affinity for a second target intact by making a point mutation in a Lib1 or Lib1_A position, and vice versa, knock out or greatly reduce affinity for said second target whilst leaving affinity for said first target intact by making a point mutation in a Lib2 position.

Example 1

Construction Of Libraries

The synthetic gene pools for libraries Lib D1L1 and Lib D1H1 were purchased from GeneArt, while the synthetic gene pools for libraries D1L2 and D1H2 were purchased from Sloning Biotechnology. All four libraries were cloned into a newly constructed phage display vector which we built from the backbone pUC19 (that was purchased from NEB) by the addition of an M13 origin; two synthetic ribosome binding sites driving expression of antibody heavy and light chains; and synthetic genes encoding two signal peptides driving secretion of antibody polypeptides into the E. coli periplasm, human CH1 and CK constant domains and a truncated C-terminal portion of M13 protein III fused to the C-terminus of the human CH1 constant domain. The libraries were transformed into TG1 E. coli cells to yield 4 libraries with transformed diversities of 109 each. From the transformed TG1 E. coli cells, the four libraries were produced as libraries of phages displaying diversified Fab fragments, using M13KO7 helper phage and standard molecular biology methods as described by (Barbas et al., Phage Display: A Laboratory Manual, Cold Spring Harbour Laboratory Press, $1^{st}$ ed., 2001; Sambrook, Molecular Cloning: A Laboratory Manual, Cold Spring Harbour Laboratory Press, $3^{rd}$ ed., 2001).

Example 2

Panning

Binders from libraries of Fab-on-phage particles can be selected in accordance with standard panning procedures (Barbas et al., Phage Display: A Laboratory Manual, Cold Spring Harbour Laboratory Press, $1^{st}$ ed., 2001; Sambrook, Molecular Cloning: A Laboratory Manual, Cold Spring Harbour Laboratory Press, $3^{rd}$ ed., 2001) against immobilized targets MBP and GST.

Example 3

Screening

Phage particles selected in Example 2 can be rescued by infecting bacterial host cells (Barbas et al., Phage Display: A Laboratory Manual, Cold Spring Harbour Laboratory Press, $1^{st}$ ed., 2001; Sambrook, Molecular Cloning: A Laboratory Manual, Cold Spring Harbour Laboratory Press, $3^{rd}$ ed., 2001). Fab protein is expressed from individual clones and tested for specific binding against the targets MPB and GST. Positive hits are used in the next step to clone bispecific constructs.

Example 4

Cloning Of Bi-Specific Antibodies

Antibody genes were designed based on the desired amino acid sequence and purchased as synthetic genes or synthetic gene fragments from GeneArt or DNA2.0. Genes encoding antibody variants with point mutations were generated by PCR or overlap PCR, using the polymerase Pwo Master, purchased from Roche, and synthetic oligonucleotides encoding the desired point mutations, purchased from Thermo Fisher Scientific, according to manufacturer's instructions. An E. coli Fab expression vector was generated by modification of the plasmid pUC19, which was purchased from New England Biolabs. The pUC19 backbone was modified by the addition of two synthetic ribosome binding sites driving expression of antibody heavy and light chains, two synthetic signal peptide sequences driving the secretion of antibody chains into the E. coli periplasm and one M13 phage origin potentially enabling single strand production. Synthetic antibody genes, synthetic fragments of antibody genes and PCR-generated variants of antibody genes encoding point mutations were cloned into this E. coli Fab expression vector by restriction digestion, using restriction endonucleases purchased from Roche, followed by ligation, using LigaFast purchased from Promega, according to manufacturer's instructions. Ligation reactions were transformed into competent TG1 E. coli cells purchased from Stratagene or Zymoresearch.

Example 5

Antibody Expression And Purification

TG1 E. coli clones bearing Fab expression constructs were grown in LB and TB solid and liquid media, purchased from Carl Roth, which were supplemented with Carbenicillin and glucose, purchased from VWR. Antibody expression in liquid cultures was performed overnight in Erlenmeyer flasks in a shaking incubator and was induced by the addition of isopropyl-β-D-thiogalactopyranoside (IPTG), purchased from Carl Roth, to the growth medium. Culture supernatants containing secreted Fab fragments were clarified by centrifugation of the expression cultures. Clarified culture supernatants were supplemented with a 1% volume of Streptomycin/Penicillin solution, purchased from PAA Laboratories, a 2% volume of 1M Tris pH8.0, purchased from VWR, and a 0.4% volume of STREAMLINE rProtein A resin, purchased from GE Healthcare. The supplemented culture supernatants were incubated on a rolling incubator for 3 hours or overnight to achieve binding of Fab fragments to the protein A resin. Resins were then transferred into gravity flow columns, washed once using 30 bed volumes of 2×PBS pH 7.4, purchased from Invitrogen, washed once using 5 bed volumes of a buffer containing 10 mM Tris pH 6.8 and 100 mM NaCl, purchased from VWR, and eluted using a buffer containing 10 mM citric acid pH3 and 100 mM NaCl, purchased from VWR. Eluted Fab fragments were neutralized by adding an 8% volume of 1M Tris pH 8.0. Neutralized purified Fab fragments were buffer exchanged into pure 1×PBS pH 7.4 (containing 1.06 mM $KH_2PO_4$, 2.97 mM $Na_2HPO_4$-$7H_2O$, 155.17 mM NaCl and no other supplements; Invitrogen catalogue No. 10010056), using illustra NAP-5 desalting columns from GE Healthcare, according to manufacturer's instructions.

Example 6

Antibody Stability Measurement

The biophysical stability of purified, buffer-exchanged Fab fragments was determined in 1×PBS pH 7.4 (Invitrogen catalogue No. 10010056) using differential scanning calorimetry (DSC). For all measurements, a capillary cell microcalorimeter equipped with autosampler and controlled by VPViewer2000 CapDSC software from MicroCal was used. All Fab fragments were scanned against pure buffer containing no antibody (1×PBS pH 7.4; Invitrogen catalogue No. 10010056). The scan parameters were set to analyze a temperature window from 32° C. to between 105° C. and 115° C., with a pre-scan thermostat of 2 minutes, a post-scan thermostat of 0 minutes and no gain. The scan rate was set to 250° C. per hour for screening applications and to 60° C. per hour for re-analysis of the most stable combination mutants. The absolute melting temperature of the Fab fragments determined in screening mode (scan-rate 250° C. per hour) was 3.7° C. to 4.5° C. higher than in re-analysis mode (scan-rate 60° C. per hour), but ranking of clones was the same in both modes. Melting temperatures of Fab fragments were determined after PBS reference subtraction, using Origin 7.0 software from MicroCal.

Example 7

Antibody Specificity Measurement

Figure 5:
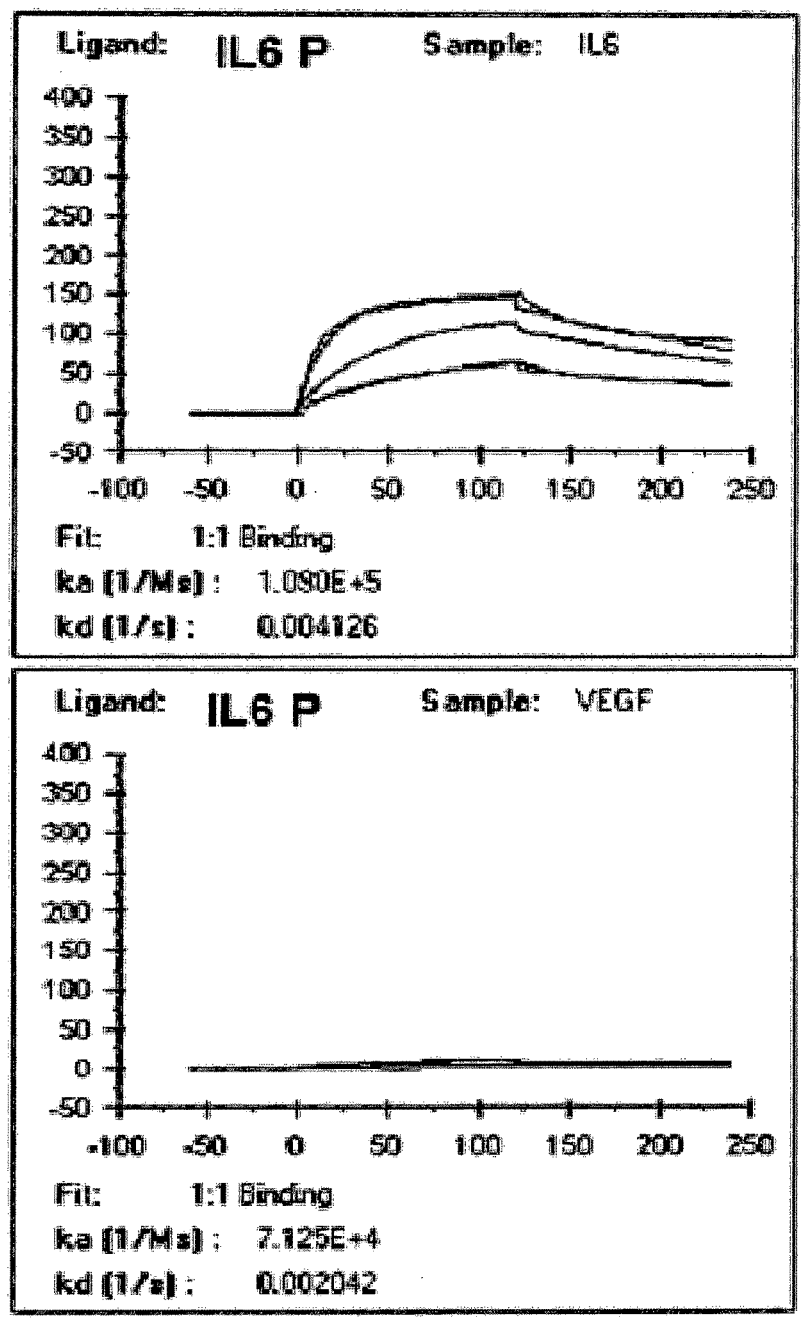
FIG. 5 shows the specificity of the antibodies disclosed in FIG. 4, demonstrated by ELISA analysis of an anti-MBP anti-GST dual targeting clone HM2LG1.
Figure 6:
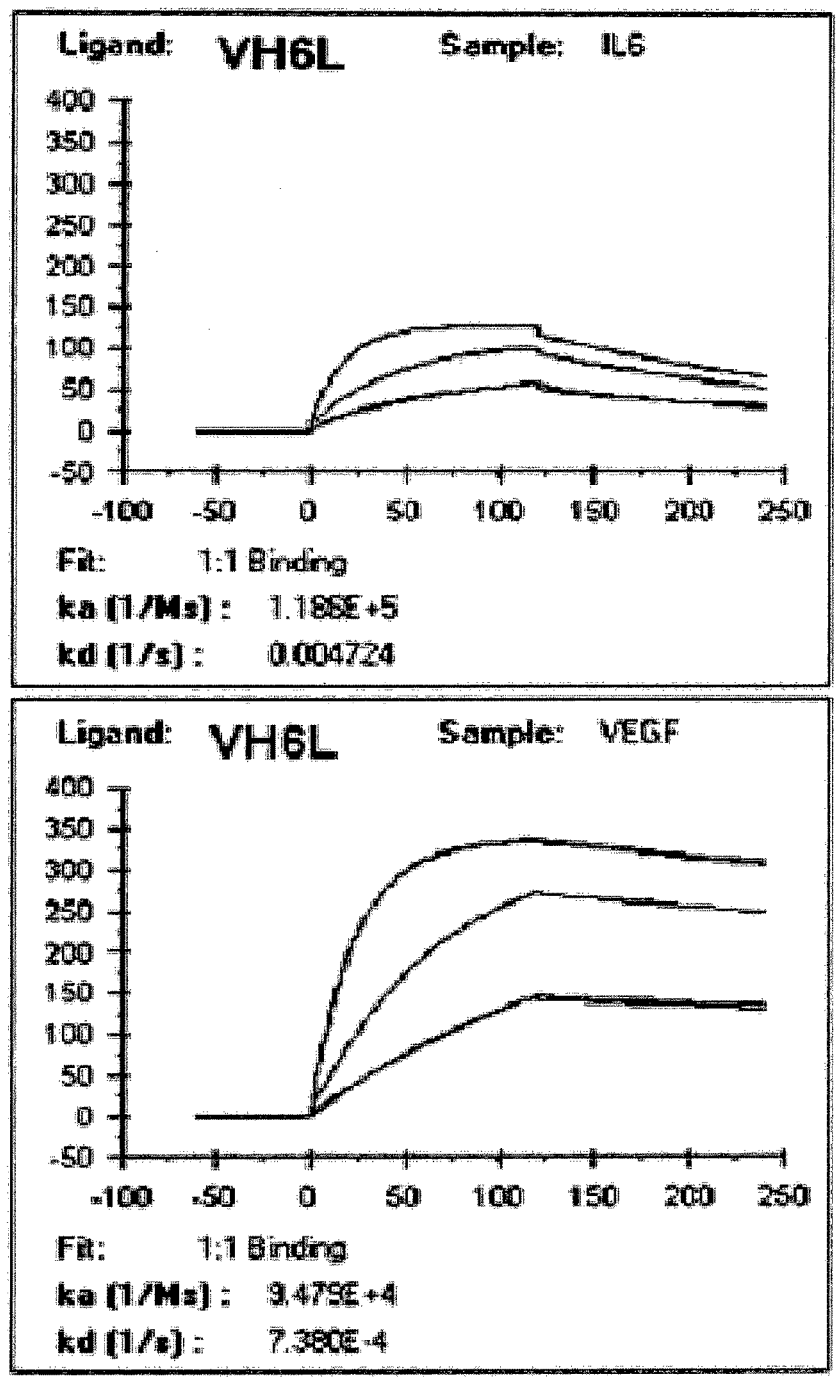
FIG. 6 shows Biacore™ data illustrating the high specificity of bispecific constructs according to the invention.

To test the specificity of antibodies selected from Lib1 and Lib2 libraries against one target and the specificity of bi-specific antibodies designed to bind both targets, Enzyme-linked immunosorbent assays (ELISAs) were performed using standard methods. Briefly, Nunc Maxisorp plates were prepared by coating with Streptavidin dissolved in 1×PBS, binding 20 nM of biotinylated targets (GST, MBP, HEL or VEGF) in PBS-T (0.3% Tween-20 dissolved in 1×PBS) and blocking with 5% skimmed milk powder in PBS-T. Thereafter, 50 µof E. coli TG1 culture supernatant expressing antibody clones as soluble Fab fragments in microtiter plates were added, followed by detection of bound Fab fragments using goat anti-human kappa light chain polyclonal antibody (Sigma) or mouse anti-Strep tag antibody (IBA) specific for a Strep-II tag fused to the C-terminus of the heavy chain in the soluble Fab expression construct. Secondary antibodies were detected using HRP-labeled tertiary antibodies, ELISAs were developed using TMB substrate (KPL), and signal was quantified using a Victor plate reader from PerkinElmer set to 450 nm. It was found that Dummy 1 Fab secreted into the E. coli culture supernatant bound none of the four targets, Fab LG1 (that had been selected from library Lib D1 L1) bound only GST, Fab HM2 (that had been selected from library Lib D1H1) bound only MBP, and Fab DT3 (that combined all the target-specific residues found in Fabs LG1 and HM2) bound only GST and MBP. None of the clones bound the control targets HEL or VEGF (FIG. 5). Experiments were performed in duplicate using two independent colonies for each Fab.

Example 8

Affinities Of Parental And Bi-Specific Antibodies

Figure 4:
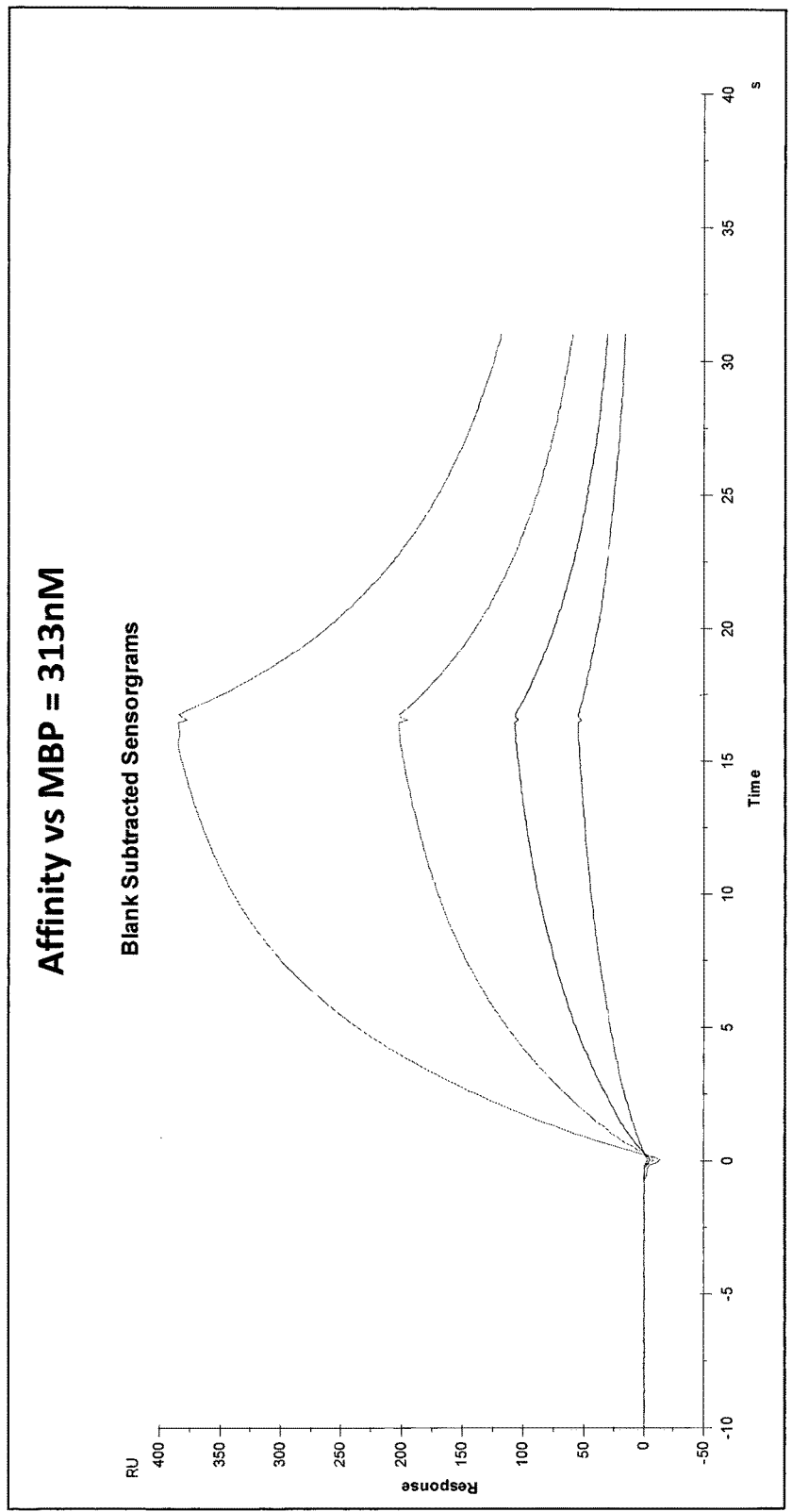
FIG. 4 gives examples of sequences of bi-specific antibodies, which were generated according to the present invention. The following SEQ ID NOs: correspond to the following sequences shown in FIG. 4: Dummy 1 VK (SEQ ID NO: 1), Dummy 1 VH (SEQ ID NO: 2), LG1 VK (SEQ ID NO: 36), HM2 VK (SEQ ID NO: 37), DT3 VK (SEQ INO: 38), LG1VH (SEQ ID NO: 39), HM2 VH (SEQ ID NO: 40), DT3 VH (SEQ ID NO: 41), IL6P VK (SEQ ID NO: 42), VEGFP VK (SEQ ID NO: 43), VH6L VK (SEQ ID NO: 44), IL6P VH (SEQ ID NO: 45), VEGFP VH (SEQ ID NO: 46), VH6L VH (SEQ ID NO: 47), GH6L VK (SEQ ID NO: 48), and GH6L VH (SEQ ID NO: 49).
Figure 7:
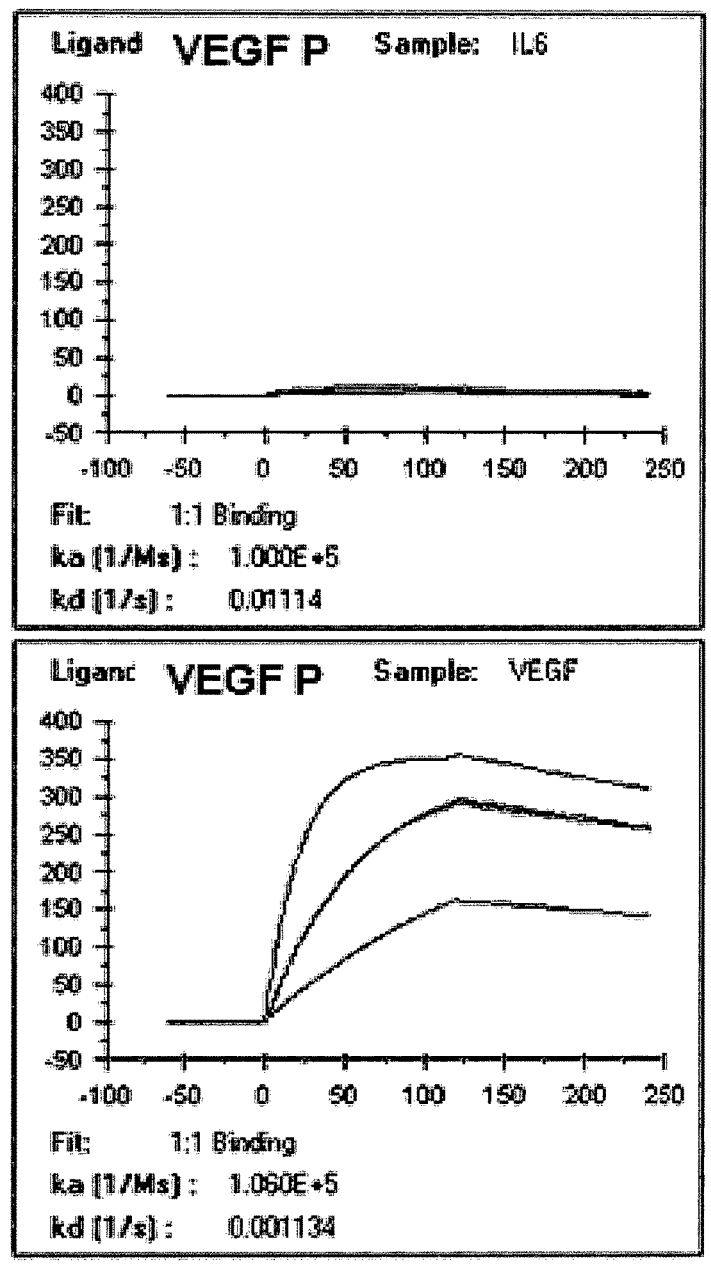
FIG. 7 shows a Biacore™ analysis of parental and bi-specific antibodies against VEGF and IL6.

Antibody libraries were selected against human VEGF (Peprotech catalogue number 100-20) and human IL6 (Peprotech catalogue number 200-06). Of the isolated parental antibody clones, IL6P and VEGFP were combined into the bi-specific antibody clone VH6L. The sequence of VH6L is shown in FIG. 4, which shows an additional point mutation at amino acid 4 of the light chain. To assess the affinities of parental and bi-specific antibodies, Biacore™ analysis was performed in order to analyze the binding behaviour of IL6P, VH6L and VEGFP. For this, an anti-light chain capture antibody was immobilized onto a CM5 chip using amine-coupling, resulting in 12000 RU. Fab fragments were captured to a level of 400-500 RU and a concentration series of IL6 and VEGF, ranging from 0 to 450 nM, was passed over the chip. As depicted in FIG. 7, clone IL6P binds to IL6, but not to VEGF, clone VEGFP binds to VEGF, but not to IL6, and the combined clone VH6L binds to both IL6 and VEGF. As shown in Table 1, the affinities to the targets are similar for the parental and bi-specific antibodies. The dissociation constant, KD, is 38 nM and 40 nM for IL6P and VH6L, respectively, and 11 nM and 7.8 nM for VEGFP and VH6L, respectively.

TABLE 1

Affinity measurements

| Ligand | Sample | ka | Kd | KD |
|---|---|---|---|---|
| IL6P | IL6 | 1.1E+05 | 4.1E−03 | 3.8E−08 |
| VH6L | IL6 | 1.2E+05 | 4.7E−03 | 4.0E−08 |
| VEGFP | IL6 | N/A | N/A | NB |
| IL6P | VEGF | N/A | N/A | NB |
| VH6L | VEGF | 9.5E+04 | 7.4E−04 | 7.8E−09 |
| VEGFP | VEGF | 1.1E+05 | 1.1E−03 | 1.1E−08 |

Example 9

Co-Binding Of Two Antigens To The Same VH-VL Variable Region

In order to demonstrate that bi-specific antibodies according to the invention can bind two different antigens simultaneously through the same VH-VL variable region, a Biacore™ experiment using the bi-specific antibody clone GH6L specific for human GMCSF and human IL6 was performed. The sequence of GH6L is shown in FIG. 4, which shows an additional point mutation at amino acid 4 of the light chain. The antibody was expressed in human IgG1 format using standard mammalian expression vectors bearing GH6L heavy and light chain and signal peptide cDNAs, by transient transfection of HEK293-6E cells. Expressed IgG was affinity-purified using protein A resin. For Biacore™ analysis, GMCSF (Peprotech catalogue number 300-03) or an anti-light chain capture antibody was immobilized onto a CM5 chip using amine-coupling, resulting in 4000 RU and 12000 RU immobilized GMCSF and anti-light chain capture antibody, respectively.

Figure 8:
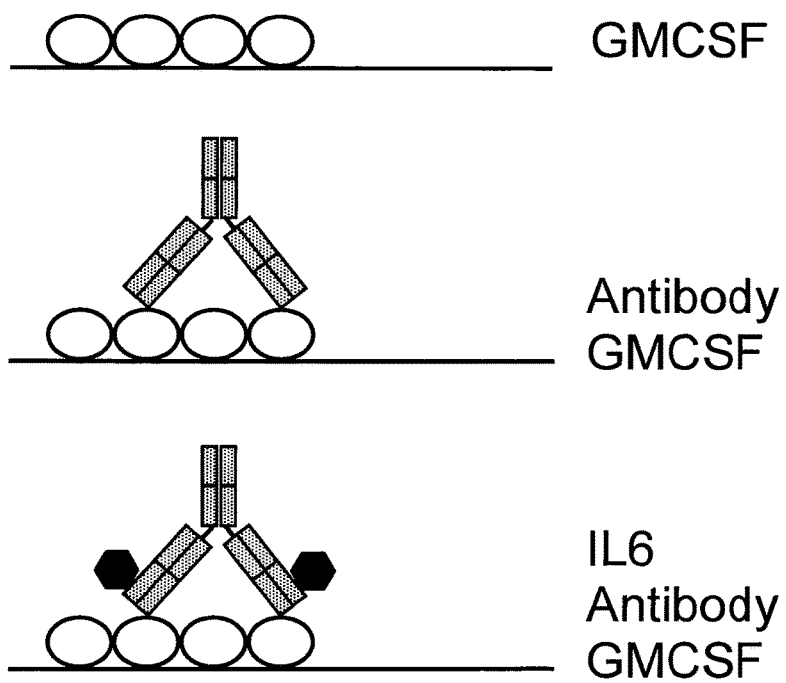
FIG. 8 shows Biacore™ data illustrating the independent co-binding of two targets to a bi-specific construct according to the invention: A: co-binding of GMCSF+Antibody+IL6; B: co-binding of anti-LC+Antibody+IL6
Figure 8:
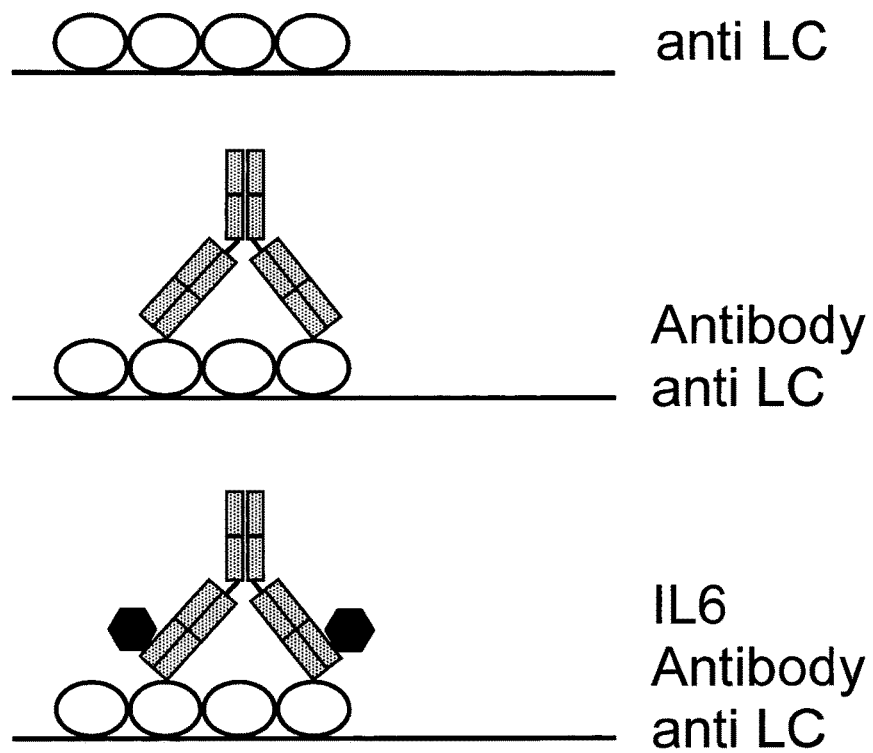

GH6L was captured onto the prepared surfaces, and in each case a concentration series of IL6 (Peprotech catalogue number 200-06) was flown over, and data were analyzed using BIAevaluation software. As can be seen in FIG. 8A, GH6L captured onto GMCSF can bind to IL6. A control experiment injecting GMCSF did not give rise to a signal showing that the IL6 binding signal was due to simultaneous binding at the same VH-VL variable region rather than binding of a "free arm" of GH6L not interacting with GMCSF on the chip surface. In FIG. 8B, GH6L is captured by the generic anti-light chain capture antibody to measure the IL6 binding affinity of GH6L without the presence of GMCSF. Comparing FIGS. 8A and 8B, it can be seen that GH6L binds to IL6 with similar affinity regardless of whether GH6L is bound to GMSCF or not.

Example 10

Independent Binding Behaviour

For several bi-specific antibodies according to the invention, the independent behaviour of the two binding sites could be shown using site-directed mutagenesis of single residues located within the Lib1 or Lib1E_A or Lib2 binding regions. In one instance, a bi-specific antibody clone directed against Target A and Target B was mutated.

By incorporating a single conservative LCDR3 point mutation H93Y within the Lib1 or Lib1E_A binding region providing the putative paratope involved in Target A-binding, affinity for Target A was largely abolished, whilst affinity for Target B was left intact.

On the other side, by incorporating a single conservative LCDR2 point mutation W56Y within the Lib2 binding region of that antibody clone providing the putative paratope involved in Target B-binding affinity for Target B was completely abolished whilst affinity for Target A was left intact.

In another instance, a bi-specific antibody clone directed against Target C and Target D was mutated. By incorporating a single conservative LCDR1 point mutation N27D within the Lib1 or Lib1E_A binding region providing the putative paratope involved in Target C-binding, affinity for Target C was largely abolished, whilst affinity for Target D was left intact.

On the other side, by incorporating a single HCDR1 point mutation L28D or a single LCDR2 point mutation Y56D within the Lib2 binding region of this second antibody clone providing the putative paratope involved in Target D binding, affinity for Target D was abolished whilst affinity for Target C was left intact.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The invention claimed is:

1. Rewrite as "A collection of antibodies or functional fragments thereof, wherein said collection comprises a diverse collection of antibody variable domain sequences wherein said antibody variable domain sequences comprise a combination of a VL domain and a VH domain, (A)
a. wherein said VL domain is based on a framework selected from SEQ-ID NOs: 1, 3, 5, and 7, wherein said VL domain is diversified in accordance with the diversification scheme shown in any one of SEQ-ID NOs: 8, 12, 18 or 19; and b. wherein said VH domain is based on a framework selected from SEQ-ID NOs: 2, 4 and 6, wherein said VH domain is diversified in accordance with the diversification scheme shown in any one of SEQ-ID NOs: 9, 13, 20 or 21;

c. provided that a combination of a VL domain based on SEQ-ID NO: 1, which is diversified in accordance with the diversification scheme shown in SEQ-ID NOs: 18 or 19, and a VH domain based on SEQ-ID NO: 2, which is diversified in accordance with the diversification scheme shown in SEQ-ID NOs: 20 or 21 is excluded; or (B)
a. wherein said VL domain is based on a framework selected from SEQ-ID NOs: 1, 3, 5, and 7, wherein said VL domain is diversified in accordance with the diversification scheme shown in any one of SEQ-ID NOs: 10, 14, 16, 22 or 23; and
b. wherein said VH domain is based on a framework selected from SEQ-ID NOs: 2, 4 and 6, wherein said VH domain is diversified in accordance with the diversification scheme shown in any one of SEQ-ID NOs: 11, 15, 17, 24, 25 or 26;
c. provided that a combination of a VL domain based on SEQ-ID NO: 1, which is diversified in accordance with the diversification scheme shown in SEQ-ID NOs: 22 or 23, and a VH domain based on SEQ-ID NO: 2, which is diversified in accordance with the diversification scheme shown in SEQ-ID NOs: 24, 25 or 26 is excluded."

2. A method for producing the collection of antibodies or functional fragments thereof according to claim 1, comprising the step of (i) expressing a collection of nucleic acid sequences encoding the collection of antibodies or functional fragments thereof according to claim 1, (ii) expressing a collection of nucleic acid sequences from a collection of vectors, particularly expression vectors, comprising a collection of nucleid acid sequences encoding the collection of antibodies or functional fragments thereof according to claim 1, and/or (iii) cultivating a collection of host cells comprising a collection of nucleic acid sequences encoding the collection of antibodies or functional fragments thereof according to claim 1, under conditions that cause or allow the expression of the nucleic acid sequences.

3. A method for identifying an antibody or functional fragment thereof with binding specificity for a target of interest, comprising the steps of contacting the collection of antibodies or functional fragments thereof according to claim 1 with the target of interest and screening or selecting for antibodies or functional fragments thereof with binding specificity for said target of interest.

4. The method of claim 3, wherein said screening or selecting is using phage display.

* * * * *